(12) United States Patent
Schmidt-Bleker et al.

(10) Patent No.: US 11,596,701 B2
(45) Date of Patent: Mar. 7, 2023

(54) DISINFECTION METHOD USING A DISINFECTION AGENT FORMED IN SITU BY REACTION OF $H_2O_2$ AND $NO_2^-$

(71) Applicant: LEIBNIZ-INSTITUT FÜR PLASMAFORSCHUNG UND TECHNOLOGIE E.V., Greifswald (DE)

(72) Inventors: Ansgar Schmidt-Bleker, Bielefeld (DE); Jörn Winter, Greifswald (DE); Klaus-Dieter Weltmann, Ostseebad Binz (DE); Hannes Bendt, Greifswald (DE)

(73) Assignee: LEIBNIZ-INSTITUT FÜR PLASMAFORSCHUNG UND TECHNOLOGIE E.V., Greifswald (DE)

( * ) Notice: Subject to any disclaimer, the term of this patent is extended or adjusted under 35 U.S.C. 154(b) by 0 days.

(21) Appl. No.: 16/950,929

(22) Filed: Nov. 18, 2020

(65) Prior Publication Data
US 2021/0069361 A1  Mar. 11, 2021

Related U.S. Application Data

(63) Continuation of application No. PCT/EP2019/062897, filed on May 17, 2019.

(30) Foreign Application Priority Data

May 18, 2018 (WO) .................. PCT/EP2018/063226

(51) Int. Cl.
*A61L 2/18* (2006.01)
(52) U.S. Cl.
CPC ......... *A61L 2/186* (2013.01); *A61L 2202/121* (2013.01); *A61L 2202/14* (2013.01); *A61L 2202/15* (2013.01); *A61L 2202/20* (2013.01)

(58) Field of Classification Search
CPC ............... A61L 2/186; A61L 2202/121; A61L 2202/15; A61L 2202/14; A61L 2202/20
See application file for complete search history.

(56) References Cited

U.S. PATENT DOCUMENTS 8,871,146 B2  10/2014  Ikawa et al.
2017/0172149 A1  6/2017  Kitano et al.

FOREIGN PATENT DOCUMENTS

EP        3346808        7/2018

OTHER PUBLICATIONS

W. Heaselgrave et al, "Acidified nitrite enhances hydrogen peroxide disinfection of Acanthamoeba, bacteria and fungi", Journal of Antimicrobial Chemotherapy.,65(6) (Mar. 23, 2010), 1207-1214.

*Primary Examiner* — Regina M Yoo
(74) *Attorney, Agent, or Firm* — JMB Davis Ben-David

(57) ABSTRACT

The invention relates to a disinfection process comprising the feed materials $H_2O_2$ and $NO_2^-$ and a mixing step and a distribution step, wherein the mixing step and the distribution step (during which each point on the surface being disinfected is wetted with a solution of active substance) are implemented during a processing period $Z_A$. An exposure step follows, in which the distributed solution of active substance acts upon the surface in contact with the solution of active substance during an exposure period $Z_E$. In this process, the maximum $NO_2^-$ concentration during the mixing step is of 300 mM, and the time-integrated reaction rate W is represented during the exposure period $Z_E$ by the integral formula (I), where $k_1$ denotes the pH-value-dependent speed constant of the reaction between $H_2O_2$ and $NO_2^-$ and the pH value of the solution of active substance before it contacts the surface being disinfected lies in the range of $2.1 \leq pH \leq 6.8$. The invention also relates to a device for providing the solution of active substance.

10 Claims, 18 Drawing Sheets

DISINFECTION METHOD USING A DISINFECTION AGENT FORMED IN SITU BY REACTION OF $H_2O_2$ AND $NO_2^-$

CROSS-REFERENCE TO RELATED APPLICATIONS

This is a continuation of International Patent Application No. PCT/EP2019/062897 filed on May 17, 2019, which claims the benefit of International Patent Application No. PCT/EP2018/063226 filed on May 18, 2018. The contents of the foregoing applications are incorporated by reference herein in their entirety.

FIELD

The present invention relates to a method and a device for disinfecting surfaces, in particular for disinfecting parts of the body, in particular hands, and/or in particular for disinfecting wounds.

BACKGROUND

The biocidal effect of the reaction products of hydrogen peroxide ($H_2O_2$) and nitrite ($NO^2$) with the addition of an acid is already known in the literature. It is also known in the literature that a variety of reactive species, including peroxynitrous acid (ONOOH) and its acid residual ion peroxinitrite (ONOO$^-$), nitric oxide (NO), nitrogen dioxide ($NO_2$), hydroxyl radicals (OH) and hydroperoxyl radicals ($HO_2$) are formed by this reaction (FIG. 1). Peroxynitrous acid in particular is assumed in the literature to be a strong biocide, but has a very short life span of only 0.8 s, which makes its use as a disinfectant problematic, since a minimum period of action must be observed to kill a sufficiently large number of pathogens.

$$H_2O_2 + NO_2^- \rightarrow \text{reaction products} \quad (1)$$

The reaction rate of the reaction (1) depends on the pH of the solution and has been investigated in various studies (Anbar & Taube, 1954; Damschen & Martin, 1983; E. Halfpenny, 1952; Lee & Lind, 1986; Lukes et al., 2015; Vione et al., 2003). The intermediate steps of the reaction (1) are not known in detail. In (Vione et al., 2003), the reactions

$$H_2O_2 + H_3O^+ \leftrightarrow H_3O_2^+ + H_2O \quad (2)$$

$$NO_2^- + H_3O^+ \leftrightarrow HNO_2 + H_2O \quad (3)$$

$$H_3O_2^+ + HNO_2 \rightarrow ONOOH + H_3O^+ \quad (4)$$

are proposed as intermediate steps for reaction (1) as a possible formation pathway for ONOOH.

FIG. 1 shows a selection of chemical processes which, according to a chemical model created in the course of the invention, lead to the formation of reactive species as a result of the mixing of $H_2O_2$ and $NO_2^-$.

But at the same time, also nitrogen oxides ($NO_x$) dissolved in water are produced by the reaction of $H_2O_2$ and $NO_2^-$. $NO_x$ are malodorous and hazardous gases. It is also known that $NO_x$ are not highly soluble in liquids and can therefore outgas from liquids. This outgassing is particularly relevant in liquid films with a large surface area. In contrast to the smaller liquid surfaces in suspension experiments, outgassing is a factor to be considered when disinfecting real surfaces and therefore makes it more difficult to use the reaction (1) for disinfection.

It has been described in the literature that mixtures of $NO_2^-$ and $H_2O_2$ are antimicrobially active and can lead to a significant reduction of microorganisms in suspension when exposed for several hours (Jiang & Yuan, 2013) or more than 15 minutes (Heaselgrave, Andrew, & Kilvington, 2010). It is assumed that ONOOH is an important component for the decontamination effect. Other antimicrobially active species, such as NO, $NO_2$, OH, and $HO_2$, are formed by the reaction of $H_2O_2$ and $NO_2^-$. It is also known that the mixing of $NO_2$ and an acid also leads to a sporicidal effect (Szabo, Adcock, & Rice, 2014). From these studies it is known that an acidification of the suspension for decontamination with $NO_2^-$ or a mixture of $H_2O_2$ and $NO_2^-$ has a beneficial effect on the disinfection effect.

The work of Heaselgrave, Andrew, & Kilvington, 2010 proposes a combination of $H_2O_2$ and $NO_2^-$ to disinfect contact lenses. In this paper the authors use a disinfecting solution containing 171 mmol $H_2O_2$ and 29 mmol $NO_2^-$ at a pH of 5. The shortest exposure time that the authors state in order to obtain a disinfecting effect is 18 minutes. For surface disinfection and particularly for hygienic hand disinfection, this exposure time would not be satisfactory. A more effective procedure can be achieved trivially by increasing the concentrations of $NO_2^-$ and $H_2O_2$. The present invention, however, is directed towards a method which, with a limited use of $NO_2^-$, enables the killing of non-enveloped viruses and bacterial spores in a likewise strongly limited time and in which no long-lasting toxicity is given.

In this context, a method is optimal with regard to the use of resources, which, under given conditions, shows the highest possible efficiency, wherein the efficiency is to be understood as a quotient of the respective effectiveness and the theoretically maximum achievable efficacy.

Lukes et al 2015 also describes the use of hydrogen peroxide and nitrite for disinfection. An experimental setup at a pH of 3.3 with 200 μM $H_2O_2$ and 90 μM $NO_2^-$ is described. Here, too, the necessary exposure time is several hours.

The same applies to WO 2011/134010 A1, which describes the use of acidified $NO_2^-$ in waste water over a period of one hour to several days.

In Ikawa et al, 2016, a disinfection method is described in which water is treated with plasma and then a bacterial suspension is added. The disinfecting effect is due to the reactive species created by the plasma. According to the study, mainly peroxynitric acid is formed here. The disinfection method of Kitano et al. is also described for surfaces in US 20170172149. It is also based on the disinfecting effect of a mixture of peroxide and nitrite. However, peroxynitric acid is formed as a disinfecting species, which is produced at pH values below 2 (pH=0). Particularly the acidic range (pH=0) is very important for the formation of the disinfecting species, so that it is sometimes necessary to raise the pH value again afterwards (to pH=4.8) in order to be able to disinfect pH-sensitive surfaces. The half-life of the disinfectant species, peroxynitric acid, is stated to be about 10 minutes at room temperature, in other documents (Lammel et al., 1990) about 3 minutes at room temperature. The disinfectant species in the present invention, on the other hand, decompose at room temperature in a much shorter time (half-lives of approx. 1 s), so that it can be excluded that these are the same active substances.

All the above-mentioned studies refer to the reduction of microorganisms in suspension using longer exposure times, particularly longer than 15 minutes. To our knowledge, however, there is no known process in which a disinfecting effect by mixing $H_2O_2$ and $NO_2^-$ already occurs within a few minutes or seconds and in which disinfection does not take place in suspension but on surfaces.

Therefore, the method described in the following aims at the decontamination of surfaces by means of mixtures of $NO_2^-$ and $H_2O_2$ in a very short time, wherein an active solution is formed by mixing $NO_2^-$ and $H_2O_2$, and is applied and/or distributed on a surface in a distribution step or spreads there by diffusion.

SUMMARY

There is therefore the problem of providing a method for surface disinfection that is based on the starting materials $H_2O_2$ and $NO_2^-$, which are applied and/or distributed on the surface to be disinfected via a distribution step, and whose total process duration is significantly shorter than with hitherto known processes based on mixing $H_2O_2$ and $NO_2^-$. At the same time, the method must tolerate surfaces with a buffering effect, keep $NO_x$ emissions as far below the concentrations assumed to be harmful to health as possible and still function reliably even if part of the $NO_2^-$ used is emitted as $NO_x$.

A further object of the invention is to provide a disinfection method in which an active solution is produced by reaction of $H_2O_2$ and $NO_2$, which can be used for disinfecting surfaces.

A further object of the present invention is the provision of a device with which the reagents necessary for use in a disinfection method with an in situ produced active solution can be stored, brought into contact and applied to the surface to be disinfected.

The object of the invention is solved by the subject of the independent method claim 1 and by the independent device claim 13. Advantageous embodiments of the method are indicated in the subclaims. These and further embodiments are described in the following.

DEFINITIONS

Figure 1:
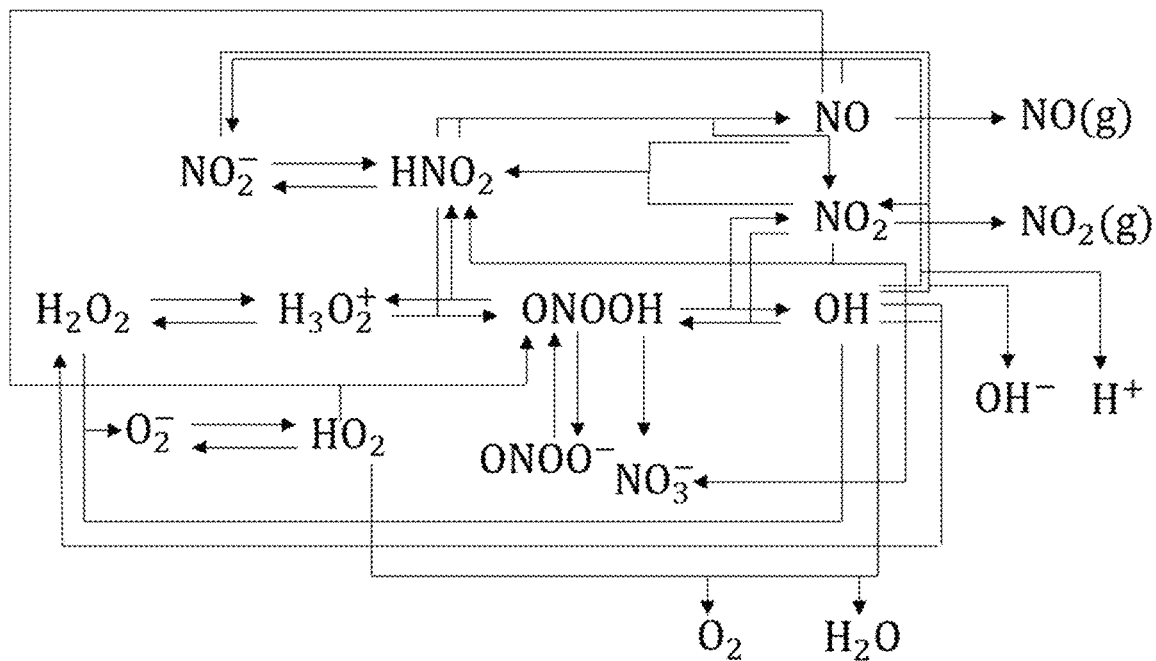
FIG. 1: Representation of the reaction scheme of the reaction between $H_2O_2$ and $NO_2^-$.

According to the present invention, the active solution comprises a disinfectant solution which is applied to the surface to be disinfected. Here, the surface means a flat surface or a surface with unevenness and/or cavities. The active solution may contain additives in addition to the disinfecting agents formed in situ. Such additives include, but are not limited to, solvents, buffer solutions, bases, fragrances, colorants and/or other disinfectants and/or ozone, as well as other reaction products and reactive intermediates of the reaction between $H_2O_2$ and $NO_2^-$.

According to the present invention, a dilution step comprises the dilution of the educts with solvents and/or additives. The dilution step precedes the mixing step or takes place at the same time as the mixing step.

According to the present invention, a mixing step comprises the mixing of educts to obtain the active solution. During the mixing step, additives can also be mixed additionally with the educts. The Mixing step can be composed of several substeps. The Mixing step starts at time $t_0=0$.

According to the present invention, a distribution step comprises the distribution of the active solution on the surface to be disinfected. Each point on the surface to be disinfected is wetted with active solution. The distribution step can start at the same time as the mixing step at time $t_0$ or can follow it.

According to the present invention, the processing period $Z_A$ comprises the mixing and distribution step, i.e. the time required to mix the educts to obtain the active solution and to wet each point on the surface to be disinfected with active solution. The processing period begins at time $t_0=0$, when the educts are first brought into contact with each other, and ends at time t1, when each point on the surface to be disinfected is wetted with active solution. The pH and temperature can change during the processing period, particularly if the mixing occurs before the first contact with the surface and the surface influences the pH and/or temperature. For this reason, the pH-value and temperature are time-dependent during the process.

Within the scope of the invention, steps relevant for the disinfection method, such as a dilution step, can also take place before the processing period, i.e. before the time $t_0=0$.

According to the present invention, an exposure step comprises the action of the active solution on the surface wetted with active solution for disinfection. The exposure step is described by the exposure period $Z_E$.

According to the present invention, the exposure period $Z_E$ comprises the time period required to achieve a sufficient disinfection effect by the active solution. The exposure period begins at time $t_1$, at which each point on the surface to be disinfected is wetted with active solution, and ends at time t2, at which each point on the surface wetted with active solution is disinfected.

According to the present invention, $NO_2^-$ is a nitrite salt with the general formula $M_xNO_2$, wherein M is an alkali or alkaline earth metal and x=1 or x=2. In particular, M is sodium or potassium and x=1. The nitrite salt may be present as a salt in solution or as a solid. Here $NO_2^-$ in solution is present as anion $NO_2^-$ or as acid $HNO_2$ depending on the pH-value.

According to the present invention, the active agents, which are the reaction products of the reaction of $H_2O_2$ and $NO_2^-$, are formed in situ. In situ means that the active agents are generated only when needed.

DETAILED DESCRIPTION OF THE INVENTION

The disinfection method of the present invention comprising at least the educts $H_2O_2$ and $NO_2^-$ consists of several substeps comprising at least
- a mixing step, where the educts are mixed to obtain an active solution;
- a distribution step in which the active solution is distributed on a surface to be disinfected, wherein the mixing step and the distribution step take place in a processing period $Z_A$ which begins at the time $t_0$ when the educts are first brought into contact with one another and ends at the time $t_1$ when each point on the surface to be disinfected is wetted with active solution, wherein $t_0$ is equal to 0 and $t_1$ is greater than $t_0$
and
- subsequently an exposure step in which the distributed active solution acts on the surface contacted with active solution over an exposure period $Z_E$ that begins at time $t_1$ and ends after the time period $Z_E$ at time t2, wherein $t_2$ represents the time at which each point on surface contacted with active solution is wetted with active solution for a sufficient time to obtain a disinfecting effect, and wherein $t_2$ is greater than $t_1$,
characterized in that
the maximum $NO_2^-$ concentration at time $t_0$ of the mixing step is 300 mM, and the time-integrated reaction rate W over the exposure time $Z_E$ is represented by the integral $$W = \int_{t_1}^{t_2} k_1 \cdot [H_2O_2] \cdot [NO_2^-] dt \geq 10 \text{ mM}, \quad (5)$$

wherein $t_1$ and $t_2$ are as defined above, and
wherein $t_2$ does not exceed 3 minutes,
wherein $[H_2O_2]$ and $[NO_2^-]$ denote the concentrations of the educts during the exposure period $Z_E$, and
wherein $k_1$ is the pH-dependent rate constant of the reaction between $H_2O_2$ and $NO_2^-$ or $HNO_2$, and
wherein the pH and the temperature may have a time dependence, and
wherein the pH of the active solution prior to contact with the surface to be disinfected is in the range of $2.1 \leq pH < 6.8$.

The pH-dependent rate constant $k_1$ can be calculated as follows $$k_1 = k_4 \frac{[H_3O^+]^2}{(K_{S,H_3O_2^+} + [H_3O^+])(K_{S,HNO_2} + [H_3O^+])} \quad (6)$$

with $$k_4 = 3.56 \cdot 10^{14} \exp\left(-\frac{E_A}{RT}\right) M^{-1} s^{-1} \quad (7)$$

$$K_{S,HNO_2} = 5.13 \times 10^{-4} \quad (8)$$

$$K_{S,H_3O_2^+} = 2 \times 10^{-2} \quad (9)$$

and the unitless quantity $$[H_3O^+] = 10^{-pH} \quad (10)$$

with the effective activation energy $E_A = 70$ kJ/mol and the temperature T. $k_4$ is 120 $M^{-1}$ $s^{-1}$ at 20° C.

The time-dependent concentrations of the educts $NO_2^-$ and $H_2O_2$ during the exposure period can be calculated using the following equations:

$$[NO_2^-] = \frac{A}{k_1}, \quad (11)$$

$$[H_2O_2] = \frac{A+D}{k_1 + rk_1}, \quad (12)$$

with $$A = -\frac{D}{1 - \exp(D(t-C))} \quad (13)$$

$$C = -\frac{\ln\left(\frac{D}{[NO_2^-]_0 \cdot k_1} + 1\right)}{D} \quad (14)$$

and $$D = [H_2O_2]_0 \cdot (k_1 + rk_1) - [NO_2^-]_0 \cdot k_1, \quad (15)$$

with $k_1$, $k_4$, $K_{S,HNO_2}$, $K_{S,H_3O_2^+}$ and $[H_3O^+]$ as described above.

$[H_2O_2]_0$ and $[NO_2^-]_0$ are the initial starting concentrations of $H_2O_2$ and $NO_2^-$ in the active solution at the time of the mixing step. These are given by the educt concentrations and the type of mixing or dilution. For example, in case of an educt concentration of 200 mM $H_2O_2$ in educt solution 1 and 200 mM $NO_2^-$ in educt solution 2 and a mixing ratio of 1:1, initial concentrations of $[H_2O_2]_0 = [NO_2^-]_0 = 100$ mM are obtained.

Furthermore is $$r = 0.11, \quad (16)$$

wherein r is an outgassing coefficient that describes the formation of $NO_x$ from $NO_2^-$ and is described in more detail below.

Figure 23:
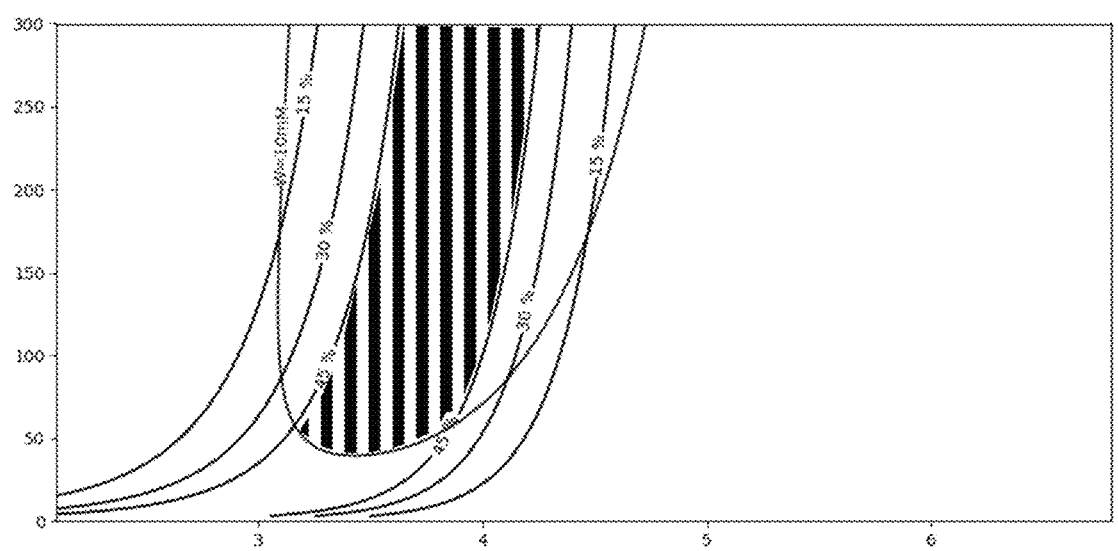
FIG. 23: Efficacy range and efficiency at a temperature of 20° C., a processing time of $Z_A=15$ s and an exposure time $Z_E=30$ s. The range above the curve marked W=10 mM indicates the range in which W>10 mM applies. The curves marked with percentages each define areas in which the efficiency has at least the specified value. The hatched area gives exemplarily those values in which W>10 mM and E>45% is valid. For x, the pH value is plotted and for y, the initial concentrations $[H_2O_2]_0=[NO_2^-]_0$ in mM.

FIG. 23 shows exemplary the efficacy ranges, which are defined by inequality (5) at a temperature of 20° C. for equal initial concentrations of $[H_2O_2]_0 = [NO_2^-]_0$, for all combinations of exposure times $Z_E$ selected from 15 s, 30 s, 50 s or 90 s and processing times $Z_A$ selected from 2 s, 15 s, 30 s and 75. This figure can be used by the expert to design the process at room temperature.

As the starting materials ($NO_2^-$ and $H_2O_2$) are converted over time, the effective reaction rate of the reaction between $H_2O_2$ and $NO_2^-$ decreases steadily. Due to the short half-life of the reaction products, these are not accumulated and therefore the instantaneous reaction rate of $H_2O_2$ and $NO_2^-$ is decisive for the efficacy of the active solution at a given time during the exposure time. For the use of the active solution as a disinfectant it is necessary that the efficacy is given for a defined minimum duration of action. Therefore, the time-integrated reaction rate W must not fall below a minimum value. The heuristic formula (5) allows the selecting applicable concentrations of $H_2O_2$ and $NO_2^-$ and a corresponding pH value for decontamination applications at a certain process temperature.

In contrast to vegetative bacteria, bacterial spores and non-enveloped viruses cannot be inactivated with alcohol-based agents or only after an insufficiently long period of time. With a reaction rate $W \geq 10$ mM not only vegetative bacteria but also bacterial spores are inactivated.

In one embodiment, the time-integrated reaction rate W of the reaction between $H_2O_2$ and $NO_2^-$ is greater than or equal to 17.

With a reaction rate $W \geq 17$ mM, in addition to vegetative bacteria and bacterial spores, non-enveloped viruses are also inactivated.

In an embodiment that is directed exclusively at vegetative bacteria, is $W = 0.3$ mM, particularly 0.5mM.

A higher time-integrated reaction rate W increases the disinfecting effect on the surface contacted with active solution.

Furthermore, the duration of the processing period and the exposure period play an important role in the efficacy of the disinfection method.

The processing period $Z_A$ includes the mixing step and the distribution step, wherein the distribution step can begin at the same time as the mixing step at time $t_0 = 0$, or can be followed by the mixing step. The processing period begins at $t_0 = 0$.

Furthermore, relevant steps can also be performed before the processing period, i.e. before the time $t_0 = 0$, e.g. a dilution step. However, these steps are not relevant for the time interval used to calculate the time-integrated reaction rate and can therefore be before $t_0 = 0$.

Subject of the invention is that the processing period ending at time $t_1$ is selected from a range of $0 < t_1 \leq 75$ s, in particular selected from the range $0 < t_1 \leq 30$ s, in particular selected from a range $0 < t_1 \leq 15$ s, in particular selected from a range $0 < t_1 \leq 2$ s.

In some embodiments, the exposure time starts after 2 s.
In some embodiments, the exposure time starts after 15 s.
In some embodiments, the exposure time starts after 30 s.
In some embodiments, the exposure time starts after 75 s.

In some embodiments, a longer processing period, which ends at time $t_1$, is necessary wherein said period is selected from a range of $15 < t_1 \leq 75$ s, in particular selected from a range $30 < t_1 \leq 75$ s, in particular selected from a range $50 < t_1 \leq 75$ s.

In some embodiments, a shorter processing period, which ends at time $t_1$, is necessary wherein said period is selected from a range of $0 < t_1 \leq 30$ s, in particular is selected from a range $0 < t_1 \leq 15$ s, in particular is selected from a range $0 < t_1 \leq 2$ s.

In some embodiments, a processing period, which ends at time $t_1$, is necessary wherein said period is selected from a range of $2 < t_1 \leq 75$ s, in particular is selected from a range of $2 < t_1 \leq 30$ s, in particular is selected from a range of $2 < t_1 \leq 15$ s.

The processing period must be large enough to wet every point on the surface to be disinfected with active solution. At the same time, however, the processing period must be selected so small that, after distribution of the active solution on the surface to be disinfected, there is still sufficient reactive active solution to achieve a disinfecting effect.

The exposure period, which begins at time $t_1$ and ends at time $t_2$, is a maximum of 90 s. A short exposure period is advantageous in order to be able to carry out the disinfection method, particularly for surface disinfection, in the shortest possible time.

In a further embodiment, the exposure period, which begins at time $t_1$ and ends at time $t_2$, is a maximum of 50 s, in particular a maximum of 30 s, and in particular a maximum of 15 s. This embodiment is particularly suitable for skin disinfection, such as hand disinfection.

The exposure period must be sufficiently long to achieve a disinfecting effect.

Furthermore, the time range (sum of $Z_A$ and $Z_E$) should be chosen sufficiently short, particularly for applications in a hand disinfection, in order to achieve the necessary disinfecting effect in a still appropriate range. A too long time period, such as over 10 minutes, is neither practicable nor reasonably applicable to hand disinfection, even in the clinical sector.

The mixing of the educts $H_2O_2$ and $NO_2^-$ to produce the active solution can take place before contact with the surface to be disinfected, or directly on the surface to be disinfected. The mixing step can be performed without external influence by diffusion and convection, be supported by mechanical distribution, or be integrated in a spraying process, in which the educts are sprayed together onto the surface to be disinfected.

Furthermore, the pH value plays a decisive role in the disinfection method according to the invention.

The pH of the active solution on the surface contacted with active solution is in the range of $2.1 \leq pH \leq 6.8$, particularly in a range of $2.5 \leq pH \leq 5$, and particularly in a range of $3.3 \leq pH \leq 4.7$.

The reaction rate between $H_2O_2$ and $NO_2^-$ depends according to (6) on the pH value of the solution. With decreasing pH, i.e. with increasing concentration of $H3O^+$, the reaction rate $k_1$ increases. At low pH-values, the disinfecting effect of the active solution is therefore higher, however, low pH-values do not allow a sufficiently long processing and exposure period due to the high reaction rate of $H_2O_2$ and $NO_2^-$ in combination with the short lifetime of the reaction products formed. At higher pH-values the reaction rate of $H_2O_2$ and $NO_2^-$ decreases significantly, but the disinfecting effect of the active solution also decreases.

In contrast to decontamination in suspensions, it was found that acidification can lead to a significant deterioration of the effect when decontaminating surfaces. This results from the necessity that the liquid on the surface must be applied and/or distributed on the surface in a distribution step and, in the case of structured and porous surfaces, must penetrate into the surface by diffusion. The active solution must not lose its disinfection effect during this time, which is however achieved by a too low pH. In this case, the educts decompose too quickly before they can develop their antimicrobial effect at any point on the surface. This problem is solved by the present invention for an active solution of at least $NO_2^-$ and $H_2O_2$ by identifying a pH range in which the use as a surface disinfectant is possible.

Figure 4:
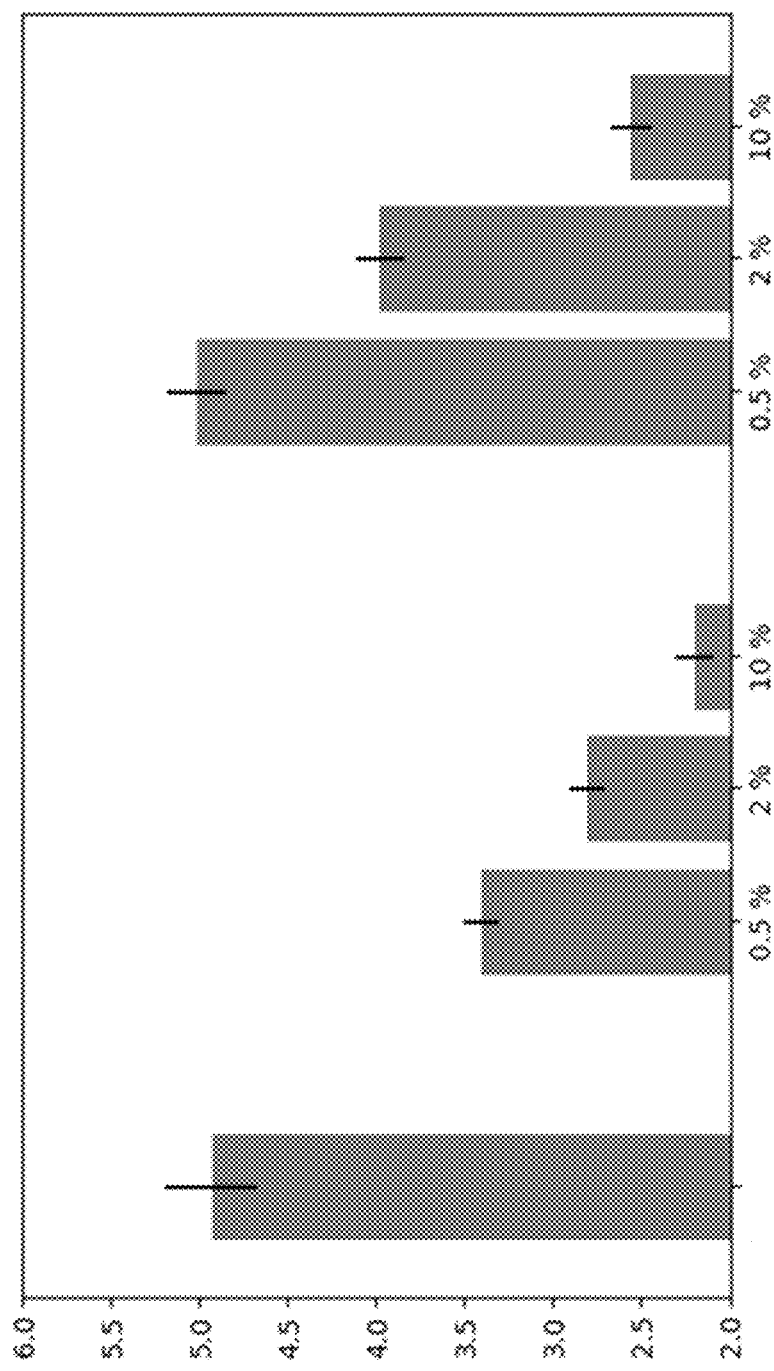
FIG. 4: pH values measured on the hand before (left) and after hand disinfection (right) according to EN 1500 with three different active solutions and in the active solutions before hand disinfection (middle). The active solutions consisted of starting solution A (50 mM $H_2O_2$ and the indicated amount of citric acid in % (w/v)), and starting solution B (50 mM $NaNO_2$).

Many surfaces have a pH regulating property themselves, particularly a buffering effect, such as the skin surface. The pH which is decisive for the method of the present invention is therefore the pH which results on the surface wetted with active solution. Such buffering surfaces and their buffering effect are known to an expert. Further details of the buffering effect of the skin in this disinfection method are shown in FIG. 4.

In one embodiment of the present invention, the disinfection method is intended to be applied to disinfecting a surface which strongly buffers the pH, in particular skin, wounds or other organic surfaces, wherein a suitable pH on the surface results from the fact that the pH value of the active solution prior to contact with the surface to be disinfected is in the range from 2.1 to 4.5, in particular in a range from 2.1 to 3.6, in particular in a range from 2.1 to 3.2.

This pH is raised by 0.2 to 1.7, in particular by 0.2 to 0.8, by contact with the buffering surface depending on the surface properties.

This means that the pH of the active solution is lower than the pH of the active solution on the surface to be disinfected. Due to this property, the educts react quickly outside the surface to be disinfected and do not accumulate in the environment. On the surface to be disinfected, particularly on the surface of a body part, particularly a hand, however, the reaction between $H_2O_2$ and $NO_2^-$ is somewhat slower due to the buffering effect of the surface, which allows the disinfecting effect to develop. Thus, the disinfecting effect remains effective for a sufficiently long time on the intended surface, on surfaces not intended for use, the educts are decomposed quickly and thus do not accumulate.

In one embodiment, the initial amounts of the educts are identical, particularly in applications when outgassing of $NO_x$ is negligible, thus $NO_2^-$ and $H_2O_2$ are completely converted. This means that no biocidal agents are released into the environment.

In one embodiment, the efficiency $E=W/W_{max}$ of the method at times $t_1$ and $t_2$, which are predetermined by the process, is at least 10%, in particular at least 20%, in particular at least 30%, wherein $$W_{max} = \min([H_2O_2]_0, [NO_2^-]_0)(\exp(-Gt_1) - \exp(-Gt_2)) \quad (17)$$

with $$G = \ln\left(\frac{t_2}{t_1}\right) / (t_2 - t_1)$$

denotes the $t_1$ maximum achievable efficacy parameter and $\min([H_2O_2]_0, [NO_2^-]_0)$ denotes the minimum concentration selected from the initial concentrations $[H_2O_2]_0$ and $[NO_2^-]_0$. This ensures that the educts used are used efficiently by the reasonable selection of the selectable process parameters pH, temperature and initial concentrations of the educts. Process parameters with different efficiency are exemplary shown in FIG. 23 for a process with $t_1=15$ s and $t_2=45$ s. The initial concentrations $[H_2O_2]_0$ and $[NO_2^-]_0$ as well as the pH were varied.

In one embodiment, the initial amounts of educts differ from each other by less than 10%, in particular the initial amount of $NO_2^-$ is 2% to 10% higher than the initial amount of $H_2O_2$. The exact value must be determined for a given application, i.e. for a given surface and amount of liquid. In this case only nitrate and water are formed as stable end products, while $NO_2^-$ and $H_2O_2$ are completely converted. This means that no biocidal agents are released into the environment. The disinfection method according to the invention is therefore particularly environmentally friendly.

A slightly higher initial amount of $NO_2^-$ compared to $H_2O_2$ is helpful to prevent the loss of effective $NO_2^-$ by outgassing of $NO_x$.

Due to the larger surface area, the outgassing of $NO_x$ is significantly higher in surface disinfection than in disinfection in solution or suspension. When the active solution is distributed over a surface, only a thin liquid film is formed, in which a large proportion of the $NO_2^-$ used can be released as gaseous nitrogen oxides ($NO_x$). This has the consequence, among other things, that up to 10% of the $NO_2^-$ introduced into the liquid is outgassed in the form of NO(g) or particularly NO₂(g). The outgassing leads to an accelerated degradation of $NO_2^-$ in an active solution of $H_2O_2$ and $NO_2^-$ on surfaces, compared to an identically prepared active solution in suspension. The outgassing influences the reaction kinetics and should also be kept low for health reasons.

$NO_x$ emissions are due to two basic processes: On the one hand, the use of an acid to adjust the pH can directly cause $NO_x$ outgassing, such as the process shown in FIG. 1:

$$HNO_2+HNO_2 \rightarrow NO+NO_2+H_2O \rightarrow NO(g)+NO_2(g)+H_2O. \quad (18)$$

The presence of $H_2O_2$ is not required for the process (18). On the other hand, the formation of ONOOH, which requires the presence of $H_2O_2$, can contribute by the reaction (19)

$$ONOOH \rightarrow NO_2+OH \quad (19)$$

to $NO_x$ emissions by subsequent outgassing of $NO_2$.

The outgassing of $NO_x$ was investigated by experiments and computer simulations. In one embodiment of the present invention, the outgassing is expressed as the outgassing rate by the formula $$R_{degas}=R_1 \times r \quad (20)$$

which can be assumed being proportional to the effective destruction rate $R_1$ of $NO_2^-$ and $H_2O_2$ by reaction (1), and contributes to the destruction of $NO_2^-$ according to the formula $$\frac{d[NO_2^-]}{dt} = -R_1 - R_{degas} = -k_1[H_2O_2][(NO)_2^-] \times (1+r). \quad (21)$$

Here, r designates a proportion related to $R_1$, which leads to the outgassing of $NO_2^-$ in form of $NO_x$. This form results from the fact that the reaction $$ONOOH \rightarrow NO_2+OH \quad (22)$$

makes the essential contribution to outgassing during surface decontamination. While r in suspension experiments is usually negligibly small, for example in the range r≤0.01, r can have values in the range r≤0.11 during surface decontamination. The concrete value depends on the respective application, particularly on the thickness of the liquid film. The outgassing that occurs therefore influences the reaction kinetics of the reaction of $H_2O_2$ and $NO_2^-$ in case of surface disinfection, which would be negligible in case of disinfection in suspension.

One possibility to limit the amount of outgassing $NO_x$ is to limit the initial concentration of $NO_2^-$.

In the disinfection method according to the invention, a maximum initial concentration of $NO_2^-$ at time $t_0$ should not exceed a concentration of 300 mM, particularly 200 mM, particularly 100 mM.

This keeps the amount of outgassed $NO_x$ as low as possible, thus minimizing harmful side effects of the disinfection method.

The disinfection method according to the invention can be used to disinfect surfaces. The disinfection method according to the invention can be used in particular for the disinfection of skin and/or the disinfection of wounds.

The disinfection method of the present invention can further be used for the decontamination of medical devices, in particular of thermolabile medical devices such as tubes of endoscopes as well as of containers and tubs.

The disinfection method of the present invention can further be used for the decontamination of seeds, crops, animal products, food, packaging as well as beverage containers or beverage lines.

In one embodiment of the disinfection method according to the invention, acid buffers or acid buffer solutions can be added to the educts and/or the active solution. For example, citrate buffers, acetic acid acetate buffers, phosphate citrate buffers, phosphate buffers or citrate buffers can be used as buffers. Buffer solutions containing citrate are particularly suitable because of their pleasant odor.

In one embodiment of the disinfection method according to the invention, additives can be added to the educts before and/or during the mixing step. Conceivable additives include, among others, solvents, bases, fragrances, dyes and/or other disinfectants, and/or ozone.

Furthermore, suspensions with non-water-soluble substances can be produced, particularly by adding fats and surfactants.

In another embodiment, one or more plasma sources can be used to produce one or more of the educts.

Thus, it would be possible to produce the educts $H_2O_2$ and $NO_2^-$ from air and water by means of electricity. In the state of the art, plasma processes are sufficiently disclosed so that the expert can select an appropriate plasma (see also Lukes et al., 2015, EP17150571.2).

In a further embodiment of the present invention, the plasma additionally produces ozone, which can be part of the active solution.

The method for disinfecting surfaces, which is the subject of this invention, is characterized in that it has a sporicidal effect. There is no approved disinfectant for disinfecting skin in Germany that also has a disinfecting effect against bacterial spores. Furthermore, the method according to the invention is low-odor and is advantageous over the common disinfection methods for disinfecting skin, e.g. alcohol, because it does not dry out the skin.

Further subject of the present invention is a device for providing the (in situ formed) disinfectant solution for and/or applying the (in situ formed) disinfectant solution to said disinfection method, consisting of
- a storage area comprising at least one reservoir in which at least one educt is retained,
- a device for mixing the educts and providing the active solution,
- a dispensing device of the active solution onto the surface to be disinfected, or
- a storage area comprising at least one reservoir in which at least one educt is retained,
- a device for dispensing the educts onto the surface to be disinfected, wherein the dispensing device is designed in such a way that the educts of the active solution are mixed on or in front of the surface to be disinfected.

The storage area and the mixing device as well as the dispensing device are fluidically connected with each other so that the educts can pass through closable openings after activation from the storage area into the mixing device and from there as active solution via the dispensing device onto the surface to be disinfected. Alternatively, the mixing of the educts can also take place outside the device by means of two nozzles directed towards each other.

The educts (at least $H_2O_2$, $NO_2^-$, and acid) can be stored and mixed in different ways. In one embodiment of the present invention, $H_2O_2$, $NO_2^-$, and an acid are each stored separately, i.e. in three separate reservoirs.

Figure 2:
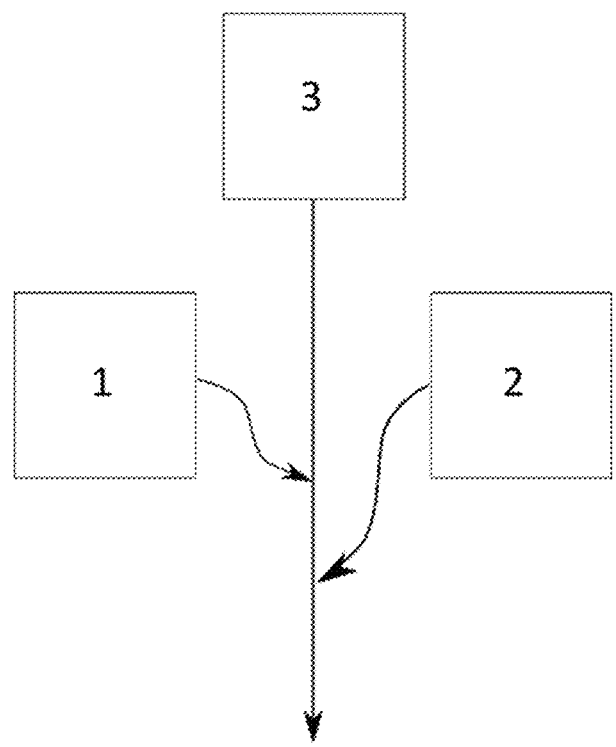
FIG. 2: Schematic representation of the disinfection method, in which the educts from the reservoirs (1, 2) are mixed with a solvent stored in another reservoir (3) to obtain the active solution.
Figure 3:
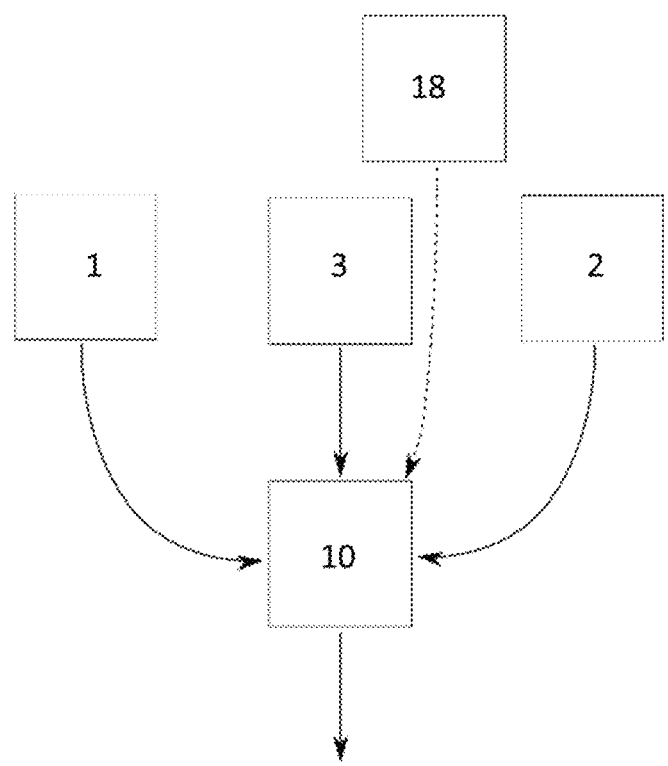
FIG. 3: Schematic representation of the disinfection method, in which the educts are expelled of the reservoirs (1,2) and mixed with a solvent, which is stored in a third reservoir (3), in a mixing area (10) to obtain the active solution. By the supply of air (18), the active solution is expelled from the mixing area and applied to the surface to be disinfected.

In a further embodiment of the present invention, $H_2O_2$ and the acid are stored together in one reservoir, and $NO_2^-$ in a second separate reservoir. In this embodiment, only two reservoirs are required to store the educts (FIG. 2).

In a further embodiment of the present invention, $NO_2^-$ is stored together with the acid, in particular nitric acid, in one reservoir, and $H_2O_2$ is stored in a second reservoir. Acidification of $NO_2^-$ with nitric acid produces $NO_x$ gases above the liquid, which lead to pressures of several bar in the respective reservoir. This pressure can be used in a further embodiment of the present invention as a drive for the device.

In a further embodiment of the present invention, both $H_2O_2$ and $NO_2^-$ are retained acidified. In this embodiment, the acidification to build up pressure and the acidification necessary for the reaction of $H_2O_2$ and $NO_2^-$ (1) can be performed independently of each other. It is possible to add the educts in different forms.

In one embodiment of the present invention, the educts can be added in the concentrations required for the efficacy of the product.

In a further embodiment of the present invention, the device may comprise a dilution area in which the educts are diluted with solvents and/or additives. In this embodiment, the educts can be added as concentrate, which is then diluted in the process. As described above, water can be used as solvent for the described process.

Conceivable additives include, among others, bases, buffer solutions, fragrances, colorants and/or ozone. In this embodiment, 3 to 200 parts of active solution can be obtained from one part of concentrate by adding the concentrate and then diluting it.

In a further embodiment of the present invention, the educts can be added as salts, which are brought into solution in the process. $H_2O_2$ is added in particular as a salt, in particular as sodium percarbonate, or in solution, while $NO_2^-$ is added in particular as a salt, in particular as a sodium or potassium salt, or in solution. The educts can be provided in different forms.

It is also possible to add $H_2O_2$ in higher concentrations, particularly in concentrations greater than or equal to 0.5% (v/v), so that $H_2O_2$ itself has a bactericidal and/or virucidal, but not a sporicidal effect. The sporicidal effect of the method performed according to the invention is then further described by the inequality (5). It is possible to provide the educts, mixed with additives or in pure form, in a respective device.

When activated, the educts and/or additives are released from the reservoirs. By mixing the educts and/or additives the active solution is formed.

Furthermore, the reservoirs can have an outlet valve through which liquid can be drained and discarded.

In a further embodiment of the present invention, the reservoirs are equipped with level sensors, in particular with mechanical level sensors or electrical, in particular capacitive, inductive level sensors, optical level sensors or ultrasonic level sensors, combined with a switch-off device which prevents the activation of the device if a minimum level of an educt is fallen below.

In addition, the replaceable reservoirs can be equipped with a device that allows the unique identification of the content and prevents the activation of the device in case of incorrect filling.

In a further embodiment of the present invention, a process control at the storage area and/or between the storage area and the dispensing device can take place by means of one or more barometers and/or one or more flow sensors, in particular combined with a shut-off device which can prevent the activation of the device in case the required operating pressure or operating flow is not maintained due to malfunction or empty storage reservoirs.

In a further embodiment of the present invention, the device comprises sensors to determine the concentration of the educts or the additives. The sensors can be in particular conductivity, capacitance or pH electrodes. Furthermore, the use of absorption spectroscopy in the ultraviolet and visible range for the determination of the educt concentrations and/or the pH value is advantageous for process control.

In particular, the device comprises a sensor or a camera which serves to dose the quantity of liquid dispensed appropriately for the respective user, wherein the control of the dispensing can be performed in particular by detecting the size of the surface to be disinfected. Furthermore, the camera and/or a sensor can be used for user or usage control. The device can comprise a microprocessor for further evaluation of these data and/or an interface for external data processing, particularly a wireless data interface. In a further embodiment, the device comprises one or more temperature sensors and/or heating or cooling elements, in particular Peltier elements, in order to ensure a constant temperature of the starting liquids and/or to temper the liquid to a temperature comfortable for the user.

In a further embodiment of the present invention, the device comprises one or more plasma sources which generate at least one of the educts, wherein the plasma source is integrated in the at least one reservoir, or is arranged upstream of the at least one reservoir, or is arranged upstream of the device for mixing the educts or is integrated in the device for dispensing the educts. The plasma sources can be used to produce $H_2O_2$ and/or $NO_2^-$ as well as to achieve a sufficient acidification of the respective liquids. In particular, a hot plasma source, in particular an arc or microwave discharge can be used for the enrichment of $NO_2^-$, as well as a cold plasma source, in particular a dielectric barrier discharge, a corona discharge or a radiofrequency discharge for the enrichment of $H_2O_2$.

Furthermore, the reservoirs can have a water inlet through which water can be added, particularly from a house connection. In particular, the device can be arranged upstream of a standard water tap or water dispenser.

In a further embodiment of the present invention, the educts are additionally diluted and/or enriched with additives in the mixing area. In a particular embodiment of the present invention, the dilution of the educts and/or the enrichment with additives takes place in a dilution area preceding the mixing area.

In another embodiment of the present invention, the mixing area may be a mixing chamber or mixing line in which the liquids are mixed. In this case the mixing line can be designed as a microfluidic mixer.

In a further embodiment of the present invention, the device has a water supply line which is fed from another reservoir or an external water connection, in particular a domestic water line. By opening a valve or by operating a pump, the water is added to dilute the active solution to the desired concentration. Here, the supply lines of the mixing area are preferably designed in such a way that the concentrated $NO_2^-$ and $H_2O_2$ solutions are diluted with water before they come into contact.

In a particular embodiment of the present invention, the mixing area and the output area are identical, so that the mixing of the educts takes place when leaving the device and/or on the surface to be disinfected.

Furthermore, the device has a compressed air supply line which is used to distribute the active solution/effective aerosol, wherein the compressed air is provided by an internal pump or a compressor or is provided externally.

Furthermore, the device has a power supply, particularly an internal battery, accumulator, solar or fuel cell.

In a further embodiment of the present invention, the device is equipped with an applicator which serves to mix and/or distribute the liquids. The applicator may consist of an aerosol generator which generates an aerosol which is distributed by an air stream, wherein the aerosol generator may be one or more ultrasonic nebulizers or one or more jet nebulizers.

In a further embodiment of the present invention, the applicator may consist of liquid pumps which convey the liquids, wherein these may in particular be hand pumps, piston pumps, diaphragm pumps, peristaltic pumps, or venturi pumps, and wherein the outlet of the applicator may be designed as a nozzle which discharges the liquid as a jet or spray. In particular, in another embodiment, at least two liquids can be conveyed with a single pump and mixed in a mixing unit before or after the pump.

In another embodiment of the present invention, the pumps are designed in such a way that all pumps are operated by a common drive. The drive may be a common shaft in the case of peristaltic pumps or piston pumps, or a common compressed air supply in the case of pneumatic pumps or venturi pumps.

In a further embodiment of the present invention, the device may comprise a water treatment plant, in particular a distillery, an osmosis filter or a carbon filter. This water treatment plant can be used in particular to purify water from a domestic water supply and to achieve a defined, in particular lower buffer capacity. This is advantageous for the process, because otherwise the pH value for the process must be adjusted by using a stronger pH buffer.

The active solution can be applied to the surface to be disinfected as an aerosol, liquid jet or steam.

Figure 11:
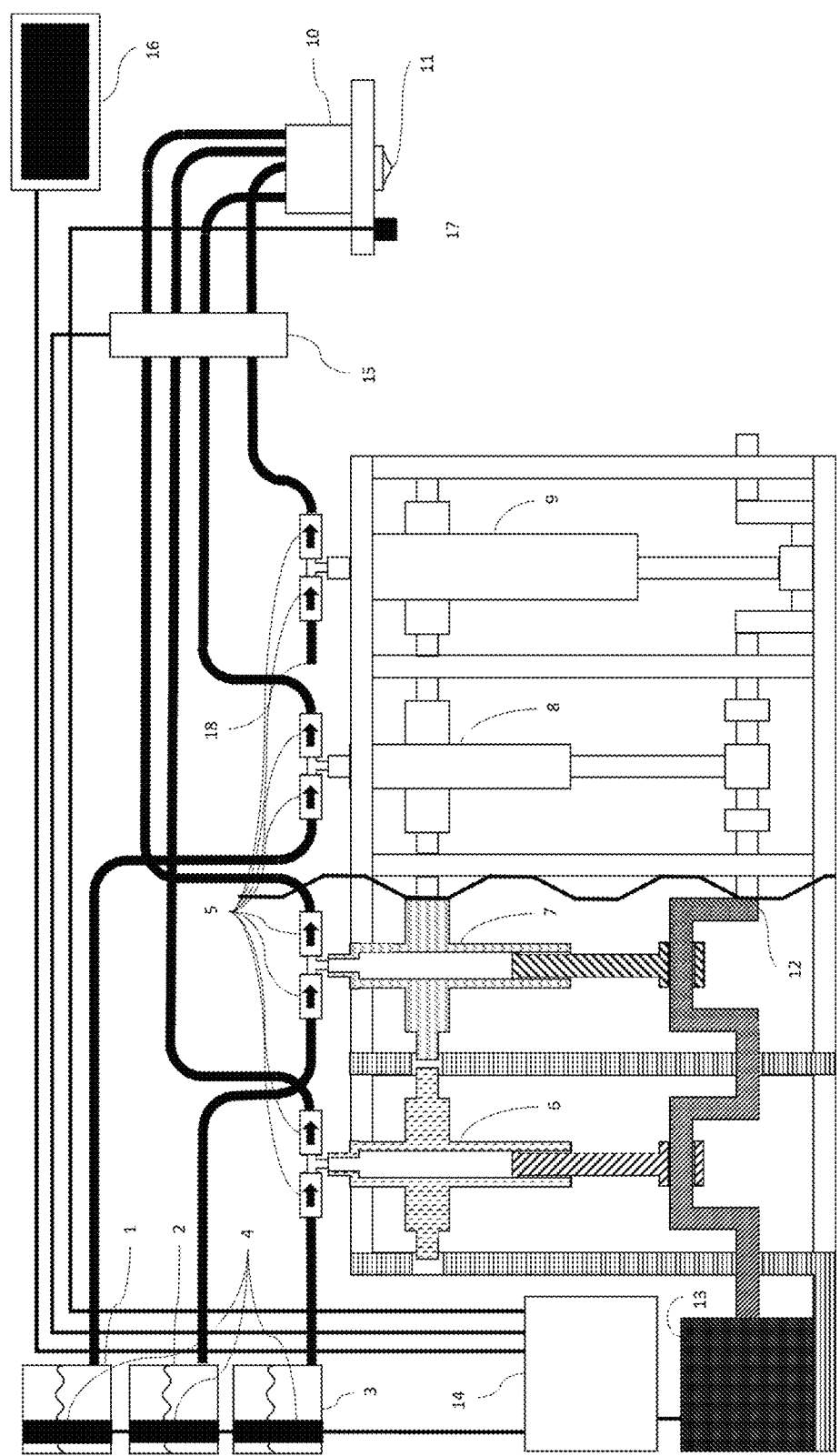
FIG. 11: Schematic representation of a device according to the invention with 2 reservoirs and a dilution liquid.

FIG. 11 shows a respective construction in which the piston pumps (6, 7, 8) for delivering the fluids are driven via a crankshaft (12). The pistons are pulled up and emptied. First, the dilution solution C is pumped from the reservoir C (3) into the piston by drawing the piston (8) up. By continuing the rotation of the crankshaft, the dilution solution C enters the mixing device (10). Check valves (5) prevent the dilution solution C from flowing back into the reservoir C (3). Due to a phase shift of 90° on the crankshaft (12), the drawing and subsequent ejection of the educt solutions A and B into the mixing device (10) is delayed in time to the provision of dilution solution C. This ensures that the mixing of the educts A and B takes place under diluted conditions. This is important, because the reaction of $H_2O_2$ and $NO_2^-$ according to equation (5) depends on the concentration of the educts and would be too fast in the concentrated case. The volume of the mixing device (10) is selected so that the sum of the individual volumes of solutions A, B and C can be taken up. The active solution is present in the mixing device (10) after addition of the reactant solutions A and B to dilution solution C. By means of the fourth piston (9), which sucks in air via the supply 18, compresses it and ejects it in the direction of the mixing device, the active solution is pressed from the mixing device into the dispensing device (11) (e.g. a nozzle) and then applied to the surface to be disinfected.

The process of educt mixing and subsequent release of the active ingredient can be continuously repeated due to the crankshaft design. The ejection frequency of the active solution can be adjusted via the rotational speed of the crankshaft (12).

By means of an optical sensor (17) it is determined without contact whether a surface to be disinfected is in the spray area and what size this area is. This information is evaluated by a control unit (14) and then the device is activated. Depending on the size of the surface to be disinfected, one or more spray pulses are emitted. In a further embodiment, the optical sensor (17) is used to identify the surface and/or the user. In this way it can be determined in a subsequent evaluation which surfaces and/or which users have received which amount of active ingredient how often and at what time.

A display unit (16) provides the user with information about the system and/or the disinfecting surface and/or the user. This includes warning messages in case of system-critical failures such as an empty reservoir or a leaking piston. By means of level sensors (4) on the reservoirs and by using pressure transducers on all supply lines to the mixing device, such sources of error can be detected.

Furthermore, the number of disinfection processes is documented and output via the display unit (16). The display unit (16) is also equipped with a module that allows all data stored by the device to be transferred to another device, preferably a computer. The reservoirs (1-3) are equipped with a coding system, which allows the clear allocation of the liquid contained in them. The control unit (14) interrupts the operation of the device in case of liquids that are not clearly identified until the intended liquid is present in the reservoir.

Figure 12:
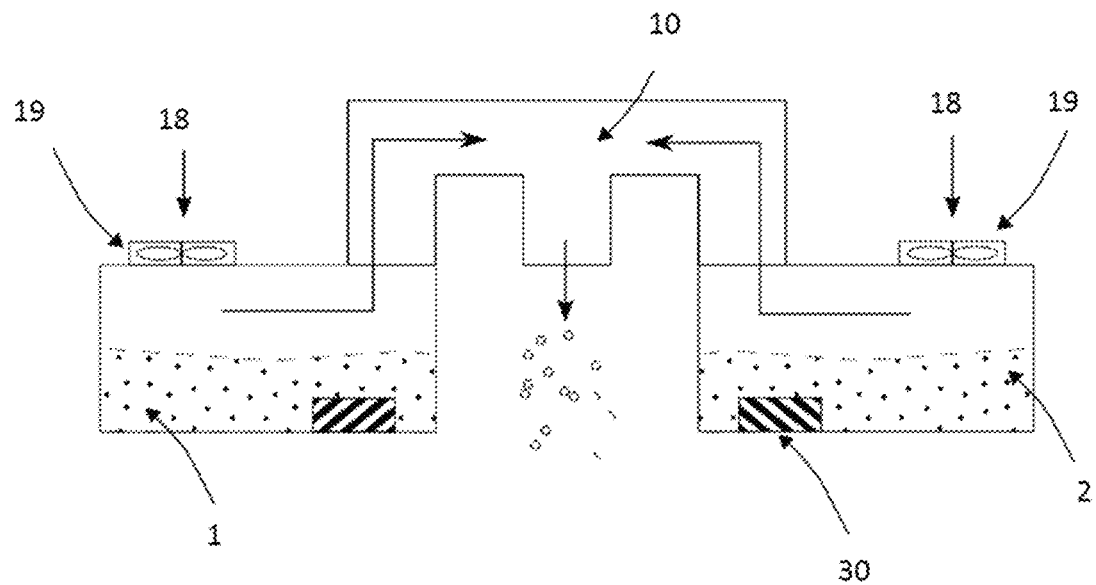
FIG. 12: Schematic representation of a device according to the invention, which provides the active solution as an aerosol.

FIG. 12 shows an embodiment of the dispensing device in which the active solution is applied as an aerosol to the surface to be disinfected. Aerosols are generated in the reservoirs (1, 2) from the educt solutions by means of an aerosol generator (30). For this purpose, fans (19) generate a circulating air flow above the educt solutions by means of an air supply (18). Liquid drops will enrich in the air stream so that aerosols are formed above the educt solutions. If necessary, the educt aerosols are led via the air stream into a mixing device (10) where the active solution is formed in the form of an aerosol. The active solution is then applied to the surface to be disinfected in the form of an aerosol.

Figure 13:
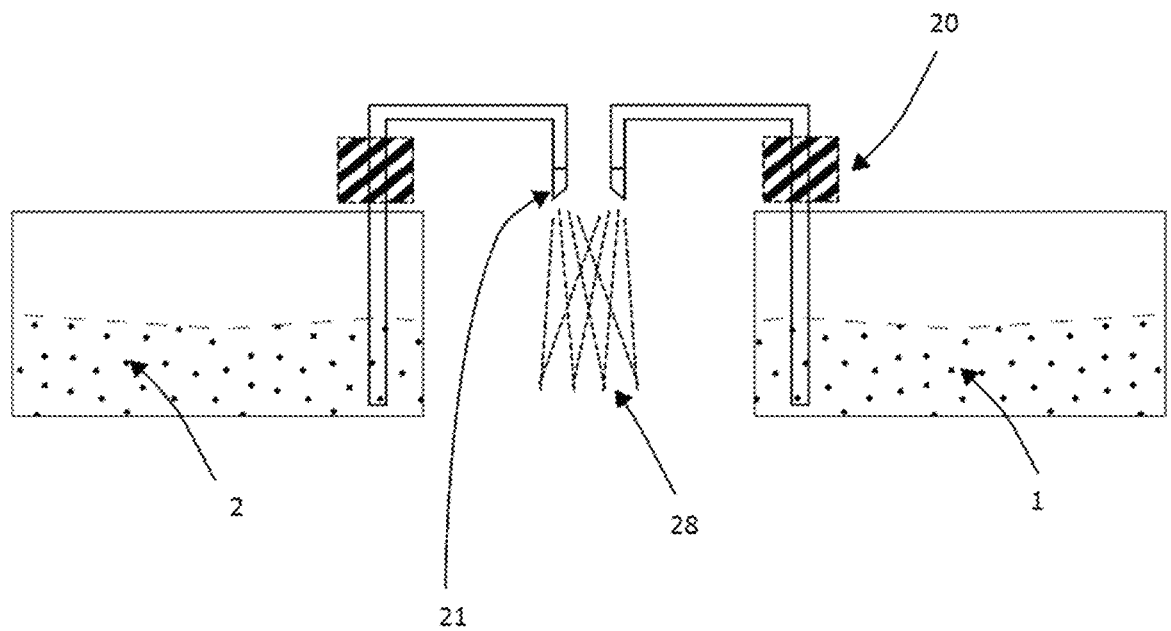
FIG. 13: Schematic representation of a device according to the invention, which provides the active solution as a liquid spray.

FIG. 13 shows an embodiment of the dispensing device in which the active solution in the form of a liquid spray is only formed on the surface to be disinfected. For this purpose, the reservoirs (1, 2) are each equipped with pumps (20). Via the respective pumps (20), the educt solutions are passed through nozzles (21) as required, so that a spray (28) is formed. In this spray (28) the educt solutions are combined and brought together on the surface to be disinfected.

Figure 14:
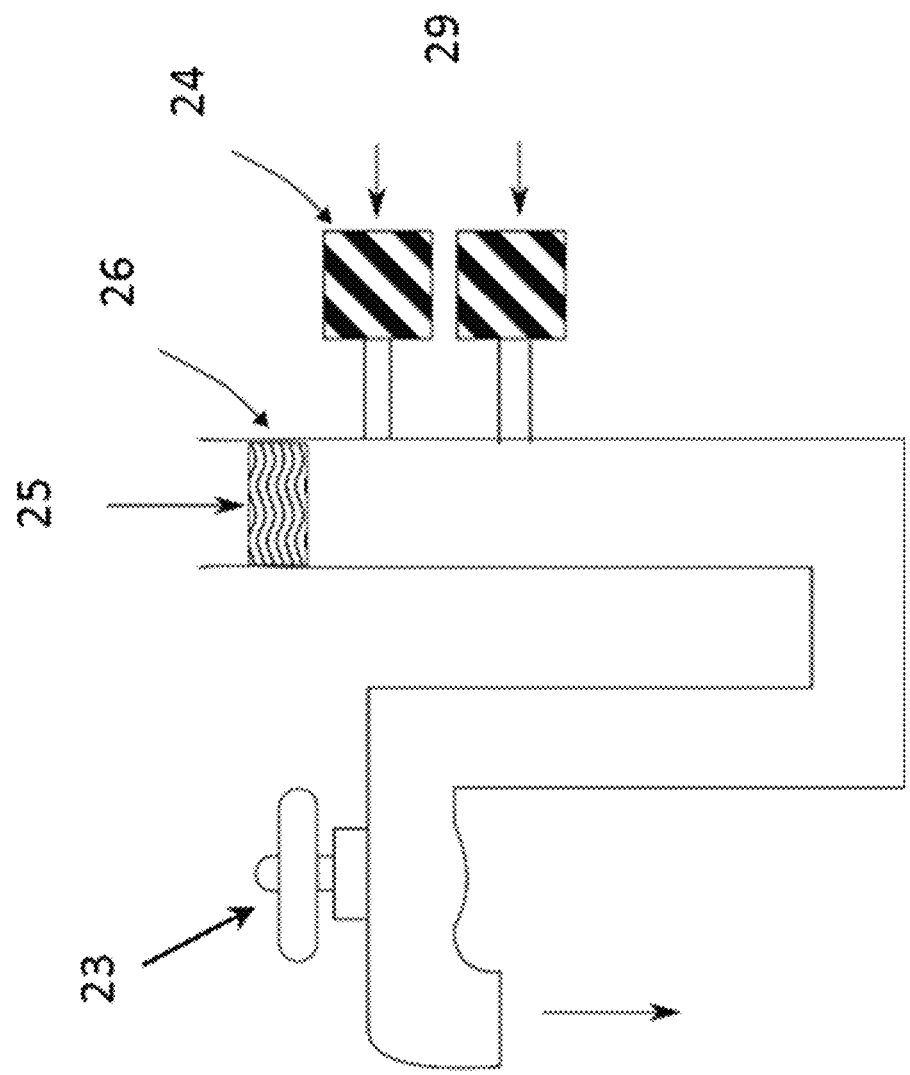
FIG. 14: Schematic representation of a device according to the invention, in which the active solution is applied via a water tap.

FIG. 14 shows a device in which the active solution is applied via a water pipe (22) using a tap (23). Pumps (24) are used to introduce the educts into the water flow (25), thus creating the active solution. A flow sensor (26) is integrated in the water pipe (22), which is used for process control and activates the inflow of the educts (29) when water flow is detected.

Figure 15:
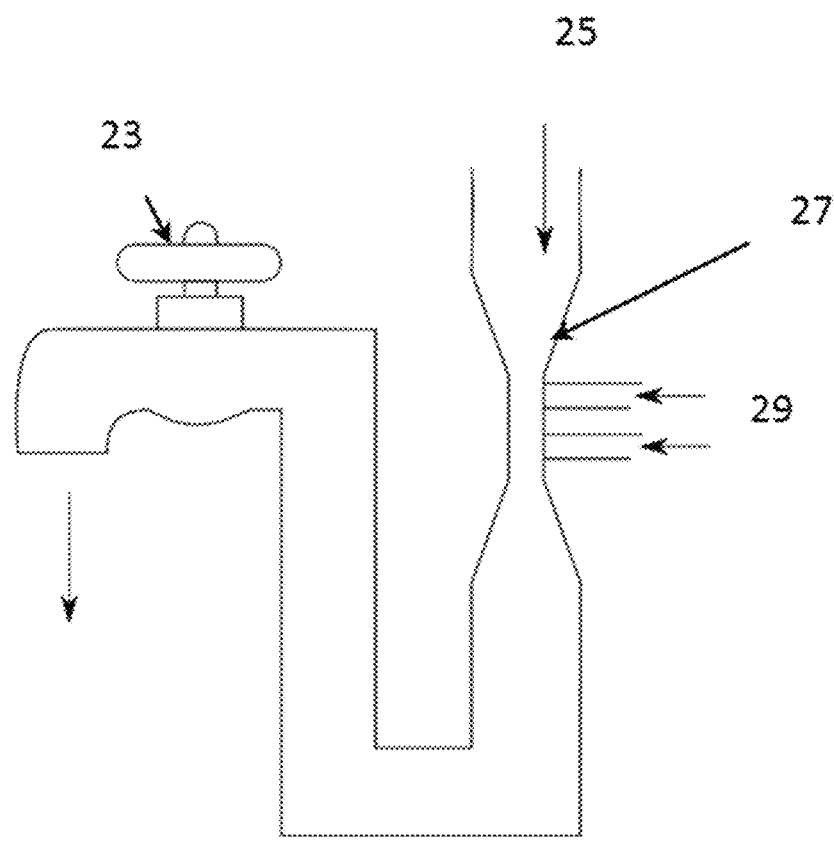
FIG. 15: Schematic representation of a device according to the invention, which is interposed in a water pipe leading to a water tap.

FIG. 15 shows a further embodiment of a device in which the active solution is applied via an inflow of educts (29) into a water pipe (25) by means of a water tap (23). In this embodiment, the educts are drawn into the water flow by a venturi pump (27), mixed in the water flow and applied as active solution via the tap (23) to the surface to be disinfected.

Figure 16:
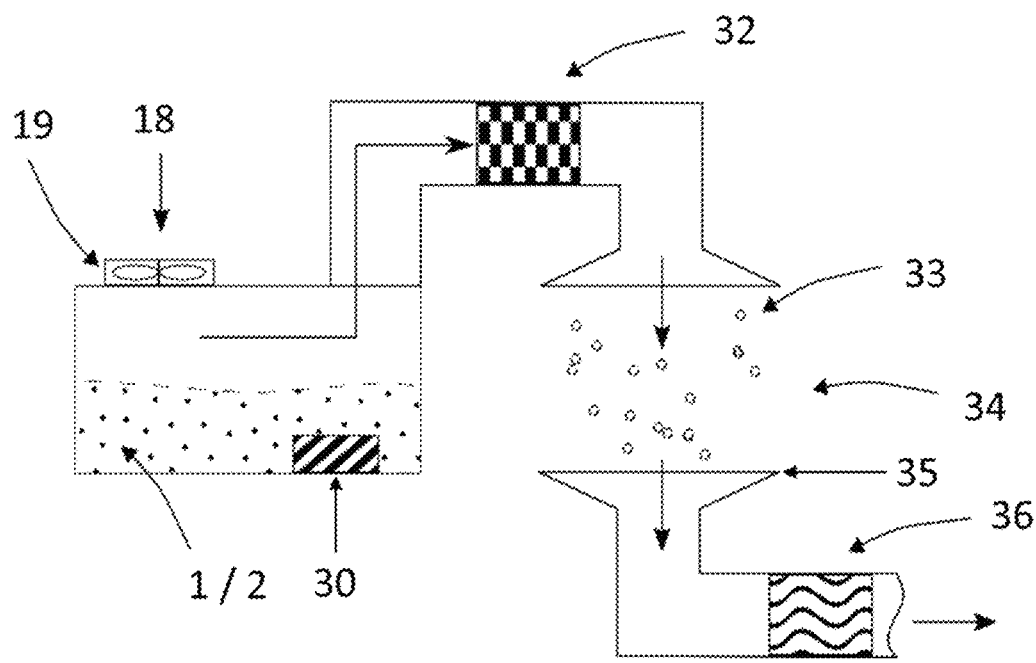
FIG. 16: Schematic representation of a device according to the invention, which contains a plasma source that generates part of the educts.

FIG. 16 shows an embodiment of a device in which a part of the educts is fed into a reservoir (1 or 2), while another part of the educts is generated by a plasma source (32) integrated into the delivery device. By means of the aerosol generator (30), the fan (18) and air supply, an aerosol is generated from the educt solution, which is then reacted with the further educt in the dispensing device by the plasma source. The resulting active solution is applied as an aerosol (33) to the surface to be disinfected in the application area (34). Furthermore, this embodiment of the device has a suction device (35), which is equipped with a filter (36), which removes harmful gaseous liquid and gaseous components from the ambient air.

Figure 5:
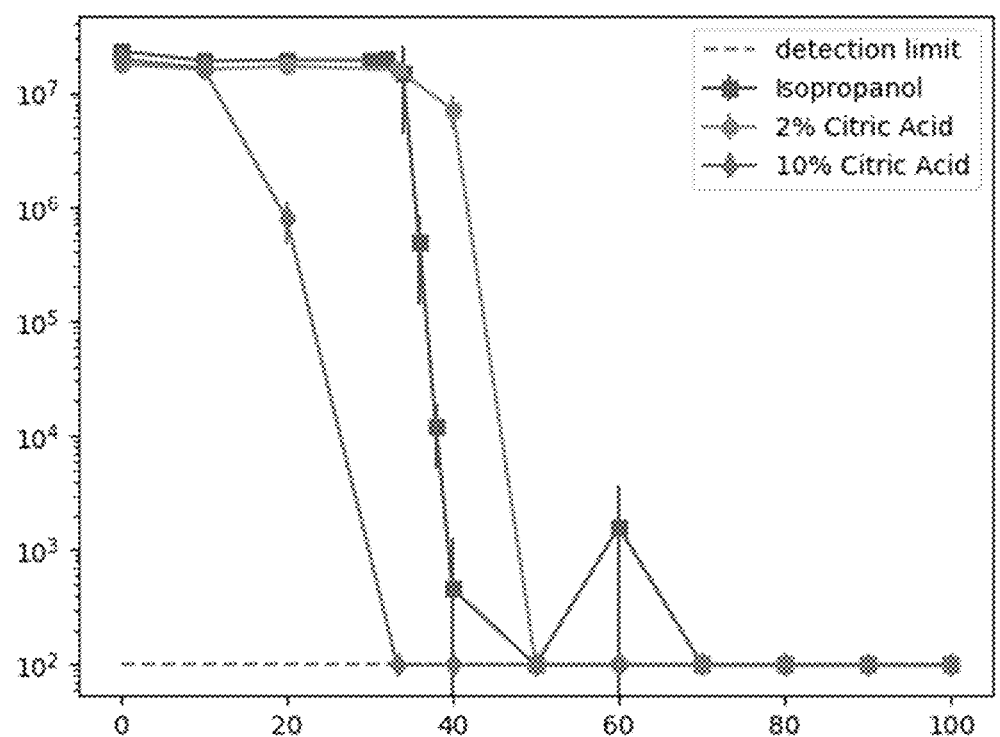
FIG. 5: Inactivation of *E. coli* in suspension with three different active solutions (isopropanol as the sole active ingredient, active solution with 2% citric acid and 10% citric acid. For x, the proportion of disinfectant in % is plotted and for y, the colony forming units.
Figure 6:
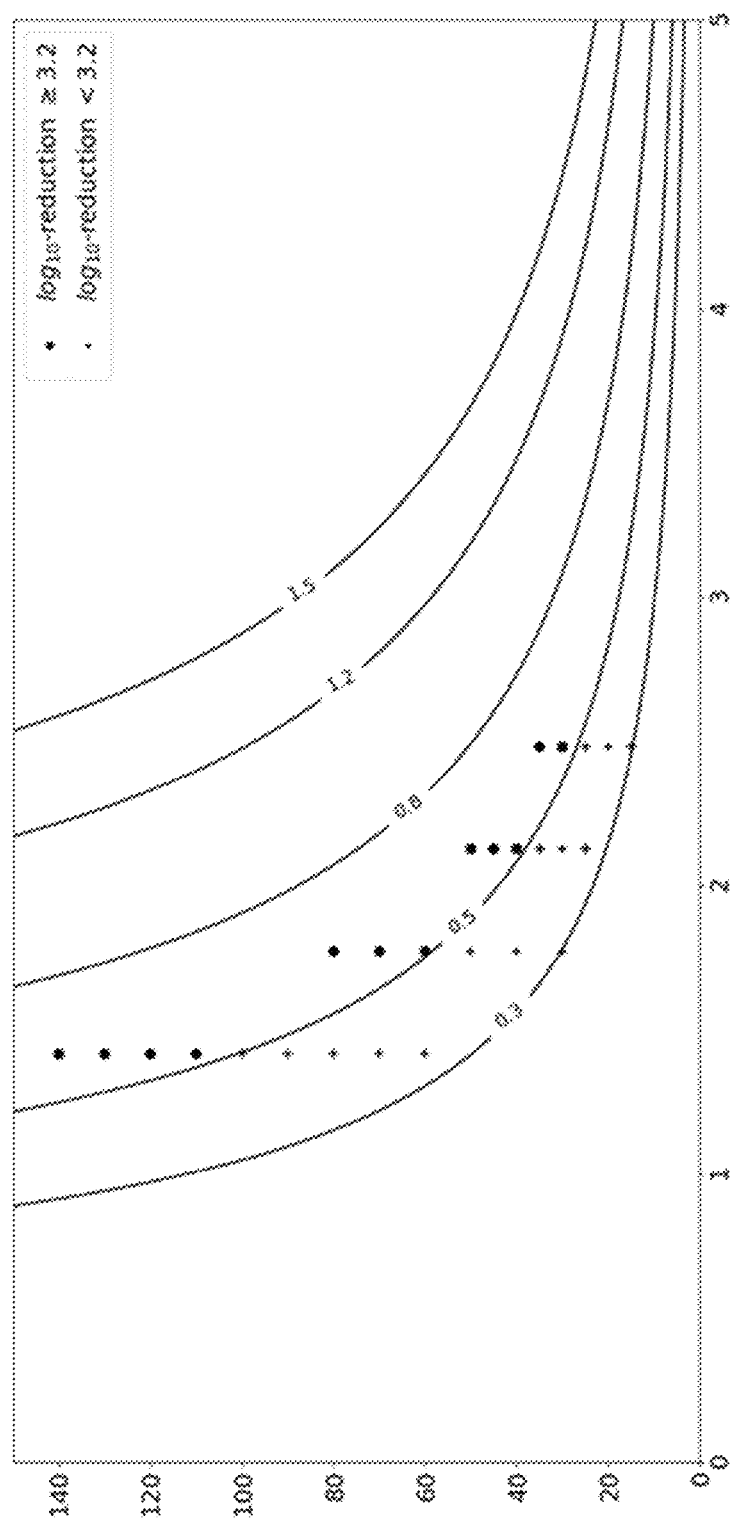
FIG. 6: Dependence of efficacy on the time-integrated reaction rate W against *E. coli* bacteria. For x, the concentration of $NO_2^-$ and $H_2O_2$ in mmol at time $t_0=0$ is plotted, for y, the reaction time in seconds. For W>0.5 mM, a reduction of at least 3.2 $\log_{10}$ steps is achieved in all experiments. For W<0.5 mM, a reduction of less than 3.2 $\log_{10}$ steps is achieved in all experiments.

LIST OF REFERENCE SIGNS (1) Reservoir educt A
(2) Reservoir educt B
(3) Reservoir dilution liquid C
(4) Level and coding electronics
(5) Check valve
(6) Piston for concentrated solution educt A
(7) Piston for concentrated solution educt B
(8) Piston for dilution liquid C
(9) Piston for generating compressed air
(10) Mixing device
(11) Dispensing device in the form of a nozzle
(12) Crankshaft
(13) Drive unit
(14) Control electronics
(15) Pressure control sensor
(16) Display unit for fill level and system status
(17) optical sensor for non-contact operation and hand size recognition
(18) Supply of air.
(19) Fan
(20) Pump
(21) Nozzle
(22) Water pipe
(23) Tap
(24) Pump for water flow
(25) Water pipe
(26) Flow sensor
(27) Venturi Pump
(28) Spray
(29) Inflow of the educts
(30) Aerosol generator
(31) Detector
(32) Plasma source
(33) Aerosol
(34) Application area
(35) Suction device
(36) Filter
Experimental Studies
Bactericidal Action The efficacy of the active solution was investigated in suspension tests. The active solution was obtained by mixing two starting liquids A and B. Starting liquid A contained 50 mM $H_2O_2$ and 2% (w/v) or 10% citric acid. Starting liquid B contained 50 mM $NO_2^-$. In order to assess the effect, the efficacy of the active solution was compared with that of isopropanol, a well-known and widely used disinfectant, as the sole active ingredient. In the test, 0.1 mL of bacterial solution (*E. Coli*) was mixed with 1 mL of a mixture of the agent to be tested and CASO-Bouillon (Casein Peptone-Soya Flour Peptone Bouillon, Carl Roth GmbH+Co. KG, Germany). The exposure time was 30 s. The CASO-Bouillon was used here for dilution as well as an artificial organic load for the disinfection experiment. The results of these experiments are shown in FIG. 5. The results clearly show that when used as a disinfectant in suspension, a stronger acidification increases the disinfection effect of the active solution. This increased efficacy with regard to the inactivation of microorganisms as a result of the acidification of a mixture of $H_2O_2$ and $NO_2^-$ is known in the literature, see (Heaselgrave et al., 2010).

Hand Disinfection Experiments

In order to test the applicability of active solution as a hand disinfectant, hand disinfection experiments were carried out according to the EN 1500 standard. The test according to the EN 1500 standard verifies how a disinfectant to be tested performs in comparison to the active ingredient isopropanol with regard to its disinfection effect. For this purpose, the hands are first immersed in a bacterial (*E. Coli*) CASO-Bouillon and then disinfected with the respective agent to be tested according to the protocol.

This test was performed with three different active solutions, with the starting liquids B each being identical and the starting liquids A each containing 50 mM $H_2O_2$, but either 0.5%, 2% or 10% citric acid.

In these tests, only the active solution with 2% citric acid was classified as more effective than isopropanol. In contrast to the disinfection experiments in suspension described above, a stronger acidification of the starting solution does not lead to an improvement but to a deterioration of the effect.

Furthermore, pH measurements were carried out during these experiments. Three types of pH measurements are shown in FIG. 5. These are the pH value of the test persons before treatment on the inside of the palm of the hand (basic value), the pH values in the mixed active solutions and the pH values on the skin after hand disinfection according to EN 1500. The latter two were tested with 0.5%, 2% and 10% citric acid concentration in active solution B.

Dependence of the Efficacy on Dose and Exposure Time

In order to establish a rule that allows to predict the efficacy of an active solution of $H_2O_2$ and $NO_2^-$, the dependence of efficacy on dose and exposure time must be known. In many cases the efficacy parameter W according to the Haber's rule as a product of dose and exposure time $Z_E$ are described. In the present case, a large number of reactive species with different lifetimes are formed, so that this dependence is not clear.

P are the reaction products relevant for the disinfection effect with concentration [P] of the process described in reaction (1). The Haber's rule now yields the Haber's efficacy parameter $$\hat{W} = \int_{t_1}^{t_2} [P] dt. \tag{23}$$

For the short-lived reaction products P, which are relevant for the disinfection effect, it can be assumed that they have a lifetime $\tau$ and have not yet decayed after a time t with the probability g (t)

$$g(t) = \exp\left(-\frac{t}{\tau}\right). \tag{24}$$

Therefore, $$Q(t) = c_1 \times k_1 [NO_2^-][H_2O_2] \tag{25}$$

is the source term of the reaction products relevant for the disinfection effect, wherein $c_1$ is the proportion, based on the reaction rate, of the reaction products relevant for the disinfection effect.

The concentration [P] can now be calculated by the convolution $$[P] = Q * g = \int Q(\tau) g(t-\tau) d\tau \tag{26}$$

Under the assumption that the lifetime τ of the reaction products relevant for the disinfection effect, which are formed as a result of reaction (1), is much shorter than the change in concentrations of $NO_2^-$ and $H_2O_2$, for example $$\left| \frac{\tau}{[H_2O_2](t=0)} \frac{d[H_2O_2](t)}{dt} \right| \ll 1,$$

g(t) can be approximated by a Dirac distribution in the form $g(t) = c_2 \times \delta(t)$ so that:

$$\hat{W} = c_1 \times c_2 \int_{t_1}^{t_2} k_1 \times [H_2O_2] \times [NO_2^-] dt \tag{27}$$

applies to the efficacy parameter W. The pre-factor $c_1 \times c_2$ in equation (26) causes only a scaling. For simplification, therefore, the efficacy parameter is defined as $$W = \int_{t_1}^{t_2} k_1 \times [H_2O_2] \times [NO_2^-] dt, \tag{28}$$

which can be used to give a necessary and sufficient condition for the efficacy of the disinfectant manufactured according to the invention. The efficacy of a mixture of $NO_2^-$ and $H_2O_2$ as a function of the efficacy parameter W thus defined was determined within the scope of the experiments underlying this invention.

Figure 7:
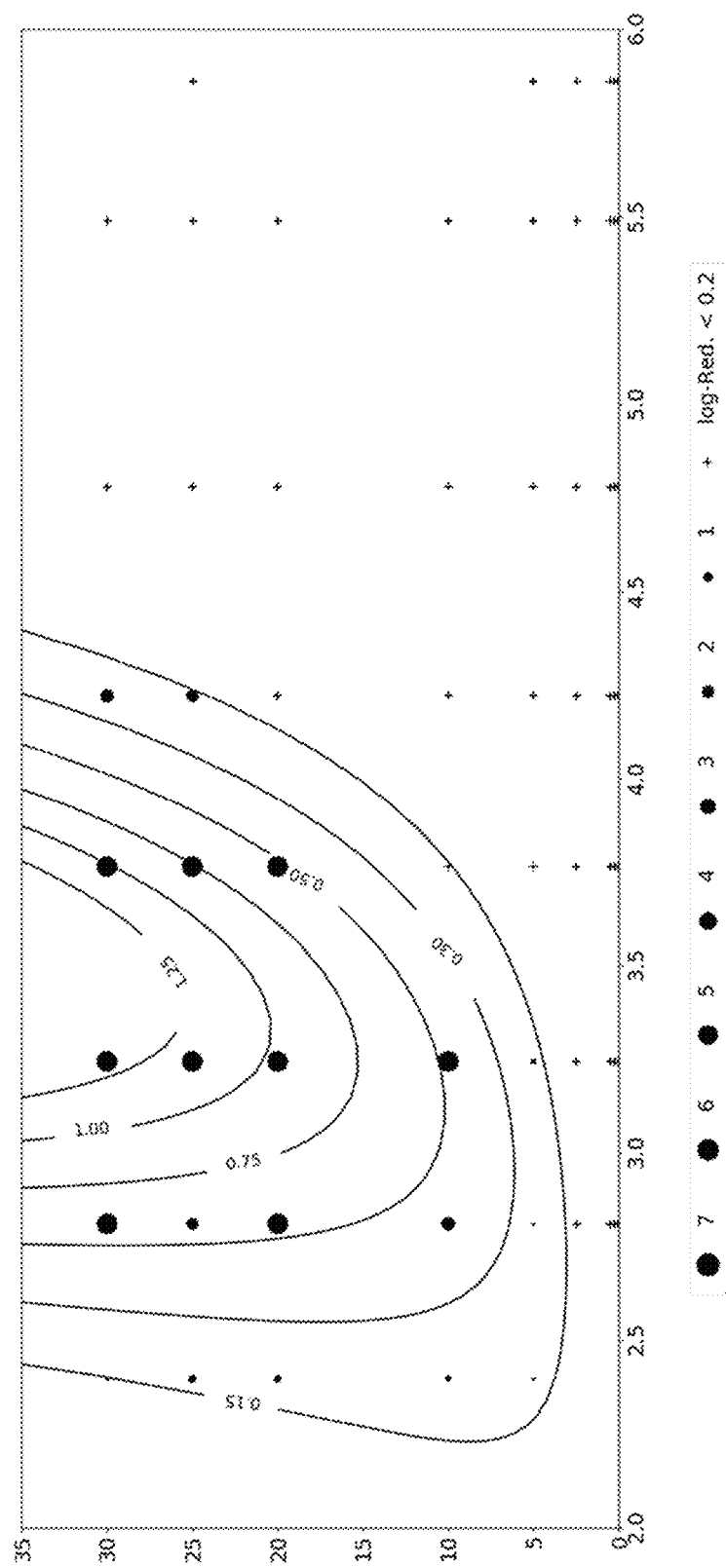
FIG. 7: Efficacy curves with constant efficacy parameter W in mM (plotted for x is the pH value and for y the initial concentration of $H_2O_2$ or $NO_2^-$ in mM at the same initial concentration, values for $t_0=0$) as well as experimentally determined log 10-reduction of bacteria (*E. Coli*) in suspension, represented by differently sized points.

The validity of equation (5) is confirmed by the following experiment:

0.22 mL CASO-Bouillon are added to a bacterial solution with a volume of 0.1 mL. This bacterial solution is exposed to an active solution consisting of $H_2O_2$, $NO_2^-$ and pH buffer for an exposure period $Z_E$, wherein the volume of the active solution is 0.78 mL. In FIG. 7, the calculated efficacy parameter is shown together with the experimental results that confirm the validity of the relation (5).

The concentrations of $H_2O_2$ and $NO_2^-$ are given by the formulas (5) to (15). Since these experiments are suspension experiments, the outgassing was neglected, so in (11) and (12) r=0 was assumed.

From the data obtained in the context of this invention it follows that for the efficacy parameter (5) in suspension for the inactivation of *E. coli* the condition W>0.3 mM, ideally W>0.5 mM, must apply in order to achieve a disinfection effect. The necessary efficacy parameters for bacterial spores and non-enveloped viruses are discussed below.

Distribution Step and Efficacy Curves

When using the active solution for surface disinfection, a distribution step must always be performed in which the active solution is applied and/or distributed on the surface to be disinfected. For example, when used as a hand disinfectant, the active solution is typically rubbed for a certain period of time, usually 30 seconds. In addition, with uneven or porous surfaces, it takes a certain amount of time for the active solution to penetrate the surface sufficiently by diffusion. Effective surface disinfection is only guaranteed if the active solution remains on the surface for an exposure time $Z_E$ after the end of the distribution step, i.e. when the surface to be disinfected is completely wetted after the processing period $Z_A$, and if it is still sufficiently effective during this exposure time $Z_E$.

According to equation (5), this is fulfilled for *E. coli* if $$W = \int_{t_1}^{t_2} k_1 \times [H_2O_2] \times [NO_2^-] dt \geq 0.3 \text{ better} \geq 0.5 \text{ mM}. \tag{29}$$

The efficacy parameter, calculated according to formulae (5) to (16), is represented by isolines for $Z_A$=30 s and $Z_E$=15 s in FIG. 7. To verify the validity of this correlation, the following experiment was performed:

0.39 mL each of two starting liquids A and B were mixed with 0.22 mL CASO-Bouillon. The starting liquid A contained 50 mM $H_2O_2$ and a buffer solution and the starting liquid B contained 50 mM $NO_2^-$. The buffer solution is used to adjust the pH value of the mixture of active solution and CASO-Bouillon. After 30 s, 0.1 mL of a bacterial suspension (*E. coli*) was added to this mixture. After an exposure time of 15 s the obtained suspension was plated out. FIG. 7 shows the resulting $\log_{10}$ bacterial reduction. As can be seen, at most a reduction of colony forming units by up to 2 $\log_0$-steps can be achieved if 0.15 mM<W<0.3 mM is given. If 0.3 mM<W<0.5 mM is given, 2 to 5 $\log_0$-steps can be achieved. If W>0.5 mM, up to 7 $\log_0$-steps are achieved. The good agreement of the experimental data with the efficacy parameter defined in (13) underlines the validity of the dose-response relation described by formulae (23)-(28) for the use of $NO_2^-$ and $H_2O_2$ as disinfectant. While the use of the method with an efficacy parameter 0.15 mM<W<0.3 mM is particularly useful as a supporting hygiene measure, for example by connecting a corresponding device upstream of a water tap, the method can be used for W>0.3 mM, better W>0.5 mM for hygienic surface and particularly hand disinfection. For a sporicidal and virucidal effect, higher values of W are necessary (see below).

Figure 8:
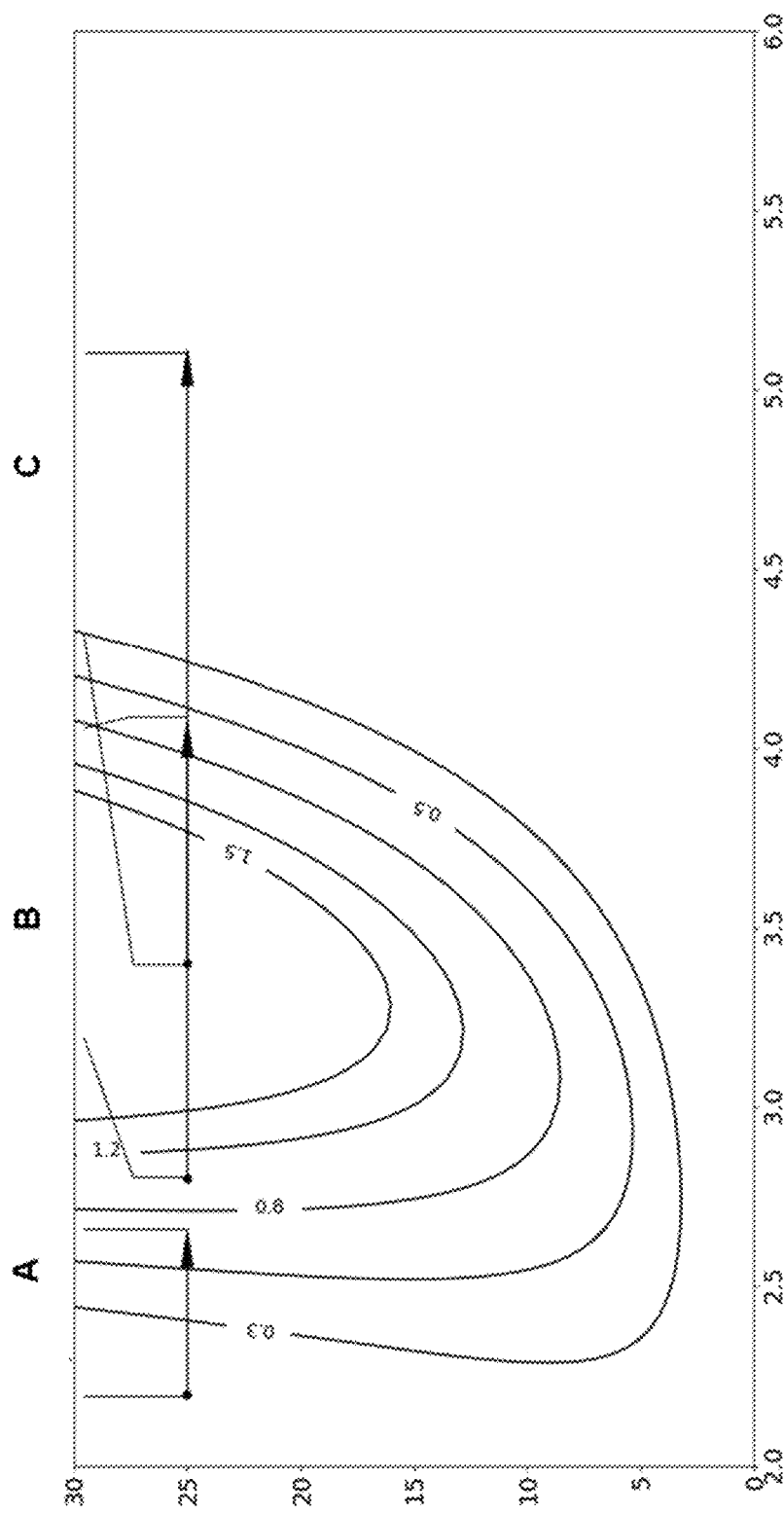
FIG. 8: Efficacy curves for surface disinfection ($t_1=30$ s, $t2=45$ s) taking into account $NO_x$ outgassing. The arrows indicate start and end pH values in the hand disinfection experiments. The initial concentration of $H_2O_2$ and $NO_2^-$ is selected to be the same (as indicated). x-axis: pH value, y-axis: initial concentration of $H_2O_2$ or $NO_2^-$ at time $t_0=0$. A: 10% citric acid, B: 2% citric acid, C: 0.5% citric acid.

In FIG. 8 the start and end pH values are also shown by arrows. These were determined by pH measurement in the hand disinfection experiments described above. The initial concentration of the educts in the active solution was $[H_2O_2]_0 = [NO_2^-]_0 = 25$ mM. The initial value is the pH value in the active solution before starting hand disinfection and the final value is the pH value of the active solution on the skin after hand disinfection according to the EN 1500 standard. In order to ensure surface disinfection in situations in which—as in hand disinfection—a pH-buffering surface is present, the temporal course of the pH value would ideally have to be known so that equation (27) can be integrated. In practical applications, however, the determination of this time dependence is often not possible. In order to be able to guarantee a reliable process nevertheless, it is sufficient, however, if—as here—the start and end pH value can be specified. Assuming that the pH value increases monotonically during the process, a sufficient disinfection effect can be guaranteed in any case if the integral (5) with both the start and the end pH value results in a sufficiently large efficacy parameter. As shown in FIG. 8, this is only the case for the active solution, where the starting liquid contains 2% citric acid (W 0.5). This active solution was the only one of the three solutions tested to pass the EN 1500 standard.

An alternative here would be to buffer the initial solution A so strongly that the pH can be kept almost constant during the process. However, this is particularly disadvantageous when used for hand disinfection, as explained below.

In these experiments the initial concentrations $[H_2O_2]_0 = [NO_2^-]_0$ were chosen. This is advantageous, because the starting materials $H_2O_2$ and $NO_2^-$ are almost completely degraded. Only $NO_3^-$ remains in the liquid in concentrations that are unproblematic in terms of health and ecotoxicity. When used as a surface disinfectant, $[H_2O_2]_0$ can advantageously be selected up to 10% lower than $[NO_2^-]_0$, so that as little $H_2O_2$ as possible remains in the decayed active solution due to the outgassing of $NO_2^-$.

It is also possible to concentrate $H_2O_2$ much higher to obtain a sufficiently large efficacy parameter at higher pH values. This can be particularly useful when applied to pH-sensitive surfaces.

Outgassing

Figure 9:
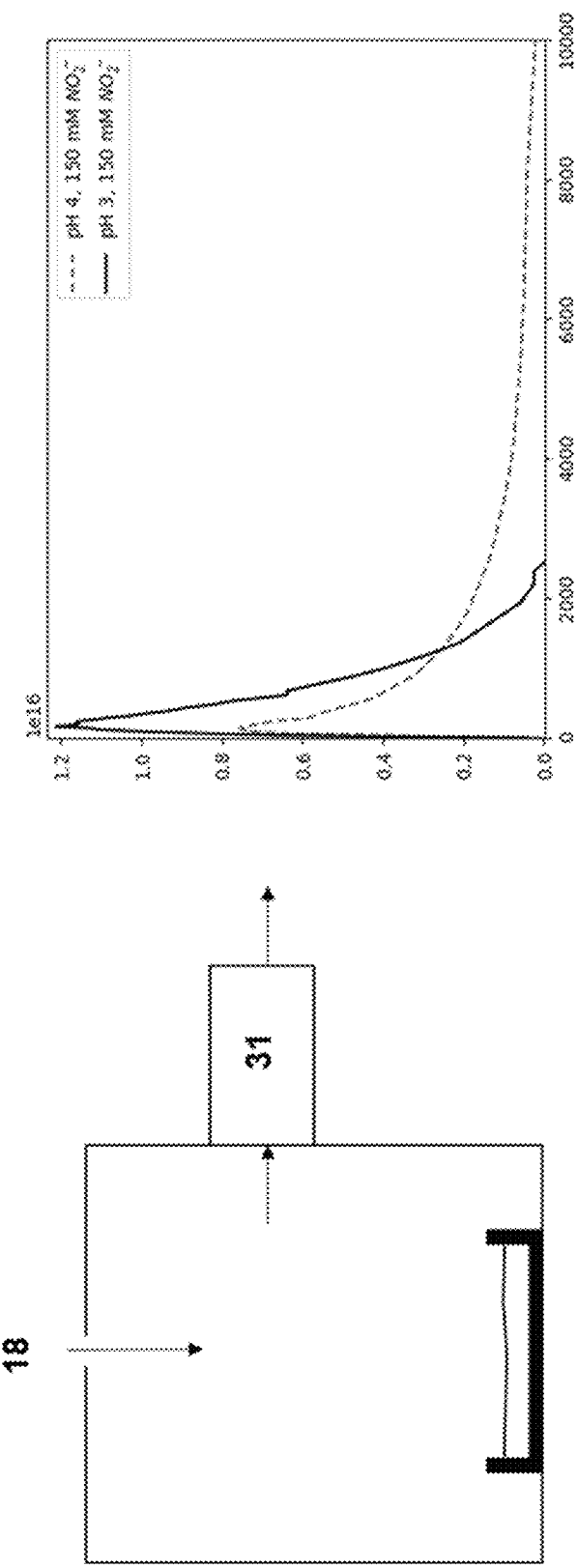
FIG. 9: Effect of different outgassing on the liquid chemistry in suspension and on surfaces. Experimental setup (left) with air supply (18) and measured concentration curve in an active solution with 150 mM $NO_2^-$ and 150 mM $H_2O_2$ at pH 3 and pH 4 (right), respectively. For x, the time in seconds and for y, the number of detected $NO_x$ molecules per second ($\times 10^{16}$) are plotted.

FIG. 9 (left) shows the measurement setup for quantifying the total amount of outgassed $NO_2$. A Petri dish was filled with 10 mL of the disinfection liquid and placed in a container in which a gas flow of 1 slm flows through. By integration of the thus determined $NO_2$ production rate (FIG. 9 right), it was determined that in this case up to 3% of the $NO_2^-$ in the liquid is outgassed as $NO_2$.

Figure 10:
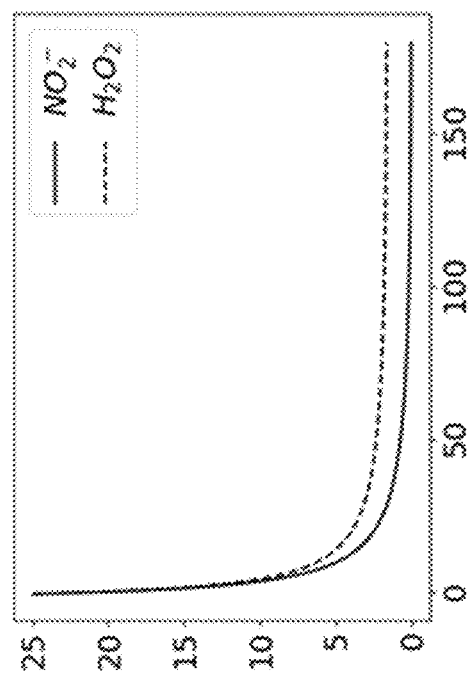
FIG. 10: Effect of different outgassing on the liquid chemistry in suspension and on surfaces. Experimental setup (left) and calculated concentration curve (right), with x time in seconds and y concentration in mM.
Figure 10:
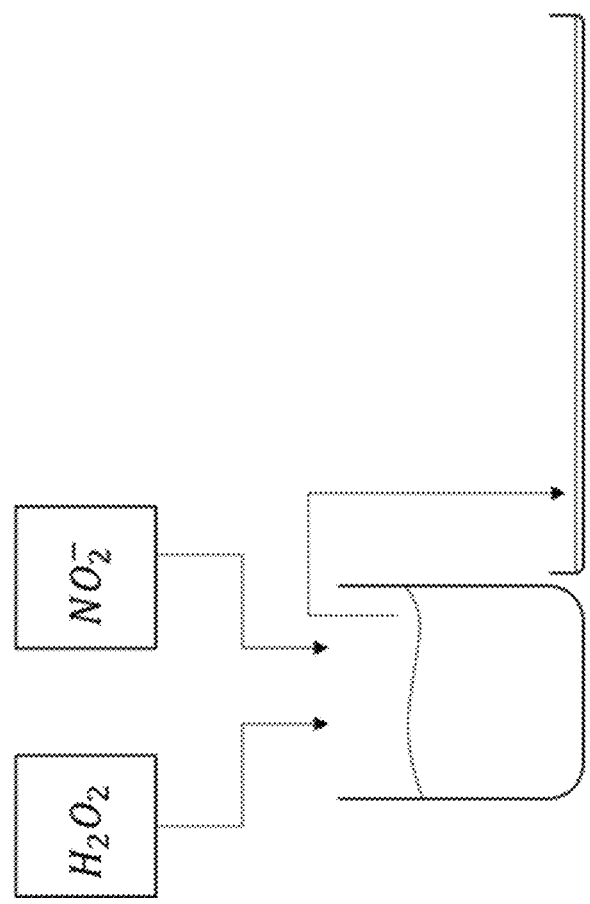

The outgassing also affects the progress of the chemical reactions in the liquid, as the following experiment shows. As shown in FIG. 10, $H_2O_2$ and $NO_2^-$ were mixed with citric acid with a concentration of 50 mM each and a volume of 3 mL each in a beaker at a pH of 2.8 for one second. Immediately thereafter, 2 mL of the mixture was added from the beaker into a flat vessel with a diameter of 15 cm to achieve a distribution of the liquid similar to a surface disinfection.

After a reaction time of 180 s, the concentrations of $H_2O_2$ and $NO_2^-$ were determined in both liquids using test strips. While in the beaker the concentrations of $NO_2^-$ and $H_2O_2$ are less than 300 μM, the concentration of $H_2O_2$ in the flat vessel is 2.5 mM, while no $NO_2^-$ is detectable. The difference in concentration allows the previously free parameter r in terms (19) and (20) to be determined for this surface application as r=0.11, which means that 9.9% (resulting from 0.11/(1+0.11)) of the introduced $NO_2^-$ will be outgassed as $NO_2$.

Based on the above-mentioned data on outgassing, it is assumed that typically up to 10% of the used amount of $NO_2^-$ can be outgassed as $NO_2$.

With a typical application amount of 3 mL of the active substance and an initial concentration of $NO_2^-$ of 300 mM in the mixed active solution, up to 118 μmol $NO_2^-$ would be released per application. In a room without ventilation with a volume of 10 m³ the MAK value would be exceeded after two applications.

Mutagenicity

An Ames test was performed to investigate the mutagenicity of the disinfection product. The test is based on the fact that a point mutation deprives an *E. coli* strain of the ability to grow in a given culture medium. By adding a mutagen, revertants are formed which are capable of growing on the culture medium. Even without the addition of a mutagen, a few revertants (natural mutagenicity) are formed by spontaneous mutations.

The mutagenicity test was performed with two solutions of 50 mM $NO_2^-$ and 50 mM $H_2O_2$, acidified with 2% citric acid. These first tests did not show mutagenicity (mutagenicity level corresponds approximately to natural mutagenicity) for the product.

pH and Temperature Dependence

If the pH and/or the temperature changes during the process, for example by applying the liquid to a buffering and/or heated surface, this must be taken into account with a time-dependent pH value pH(t) or a time-dependent temperature T(t) when evaluating the densities (equations (11) and (12)) and, accordingly the integral (5). In particular, the integral (5) can be calculated stepwise for corresponding temperatures and pH values in successive process steps. UV spectroscopy is particularly suitable for the measurement of changes in pH in suspension. For this purpose, the pH value can be determined from the ratio of $NO_2^-$ to $HNO_2$ in the liquid. Common pH probes are also applicable. The pH measurement of the liquid applied to a surface can also be realized by using appropriate pH probes. For pH surface measurements, a pH surface electrode from Mettler-Toledo International Inc. (pH electrode InLab Surface) was used in the hand disinfection experiments described in this specification. A wide variety of methods are available for temperature measurement. The temperature values given in this specification were determined using a fiber-optic temperature sensor with fast response time and low heat capacity (FOTEMP1-OEM from Weidmann Technologies Deutschland GmbH).

Figure 17:
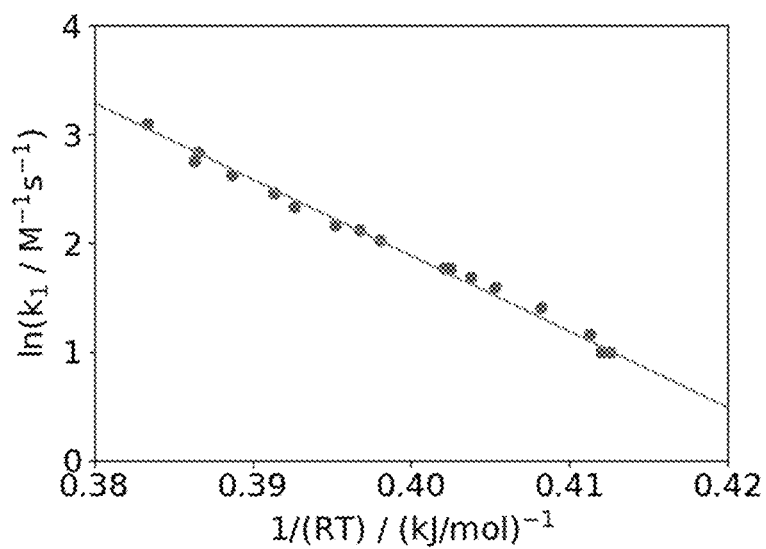
FIG. 17: Arrhenius graph for the reaction of $NaNO_2$ and $H_2O_2$ with an initial concentration of 5 mM for each educt using a citric acid-phosphate buffer at pH 3 between 0° C. and 40° C.

The temperature dependence of the reaction coefficient $k_1$ was determined by UV absorption spectroscopy. The reactants $NaNO_2$ and $H_2O_2$ were reacted at temperatures between 0° C. and 40° C. using a citric acid-phosphate buffer. The reaction rate was determined by time-resolved quantification of the densities of $NO_2^-$ and $HNO_2$. Initial concentrations of $H_2O_2$ and $NO_2^-$ of 5 mM each were used to determine the reaction rates. FIG. 17 shows the corresponding Arrhenius graph. The temperature-dependent reaction coefficient is $$k_4 = 3.56 \cdot 10^{14} \exp\left(-\frac{E_A}{RT}\right) M^{-1} s^{-1}$$

with the effective activation energy $E_A$=70 kJ/mol

No Formation of Peroxinitrate

The experiments described below show that no peroxinitrate is produced when the disinfection method according to the invention is performed.

Figure 18:
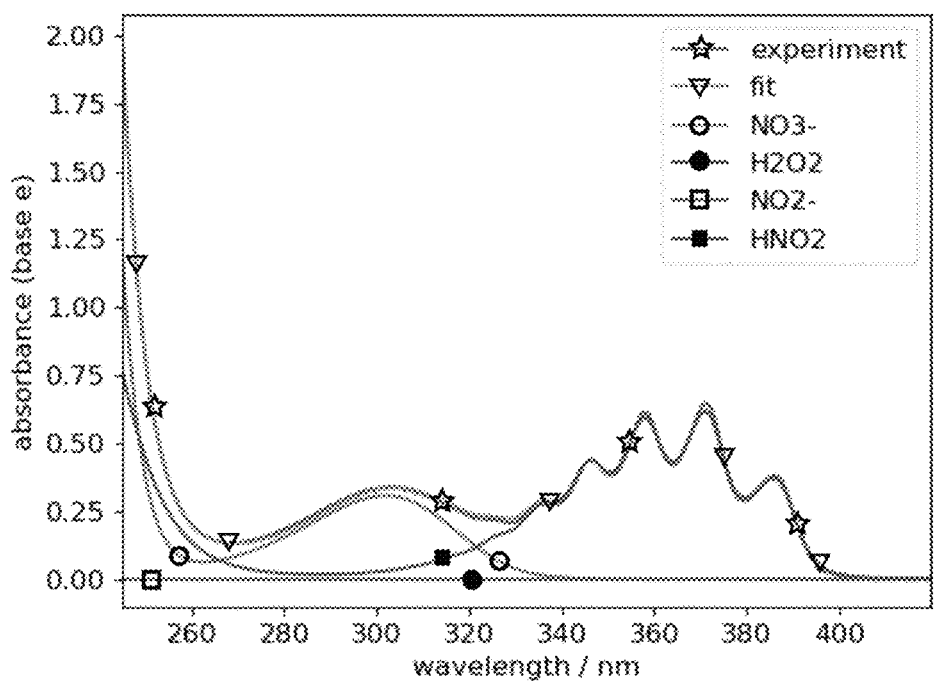
FIG. 18: Measured absorbance and corresponding fits of the reaction products $NO_3^-$, $H_2O_2$, $NO_2^-$ and $HNO_2$ from the reaction of 73.2 mM $NaNO_2$, 58.9 mM $H_2O_2$ and 100 mM HCl at 0° C. after 5 min reaction time.

In the ice bath, reaction solutions of 73.2 mM $NaNO_2$, 58.9 mM $H_2O_2$ and 100 mM HCl were cooled to 0° C. 1 mL each of the reaction solutions were mixed in a reaction vessel (also in the ice bath). The hydrochloric acid was used to lower the initial pH value of the mixture to 2.1. After 5 minutes in the ice bath the reaction products were quantified by UV spectroscopy. The measured absorbance Aexp=−ln (I/I0) is shown in FIG. 18. I0 and I represent the measured intensities before and after passing through the test medium. To quantify the reaction products, the concentrations [i] wavelength-dependent effective cross sections $\sigma_i(\lambda)$ of the species i∈{$NO_2^-$, $HNO_2$, $NO_3^-$, $H_2O_2$} in the wavelength range 250 nm≤λ≤420 nm were varied using the method of least squares using the model function ("fit") A=$\Sigma_i[i]\sigma_i L$, resulting in the best fit between model function A and experimentally determined absorbance $A_{exp}$. After 5 minutes reaction time, 19 mM $NO_2^-$ and 4.8 mM $HNO_2$ are thus determined in the mixture. $H_2O_2$ and $NO_2^-$ were not detected. It can also be excluded that peroxinitrate was formed, which absorbs in the range of 230-280 nm (Loegager & Sehested 2005). The results are stoichiometrically consistent with the reaction mechanisms described by reactions (2) to (4).

Figure 19:
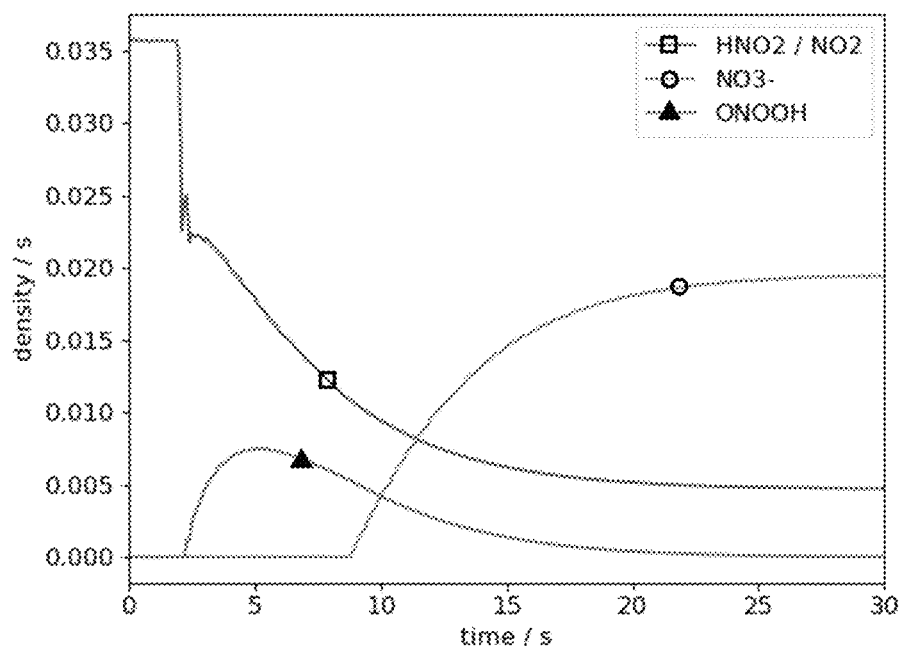
FIG. 19: Time-resolved measurement of the densities of $HNO_2/NO_2$ (total density of $HNO_2$ and $NO_2^-$), $NO_3^-$ and ONOOH in the reaction of 73.2 mM $NaNO_2$, 58.9 mM $H_2O_2$ and 100 mM HCl at 0° C.
Figure 20:
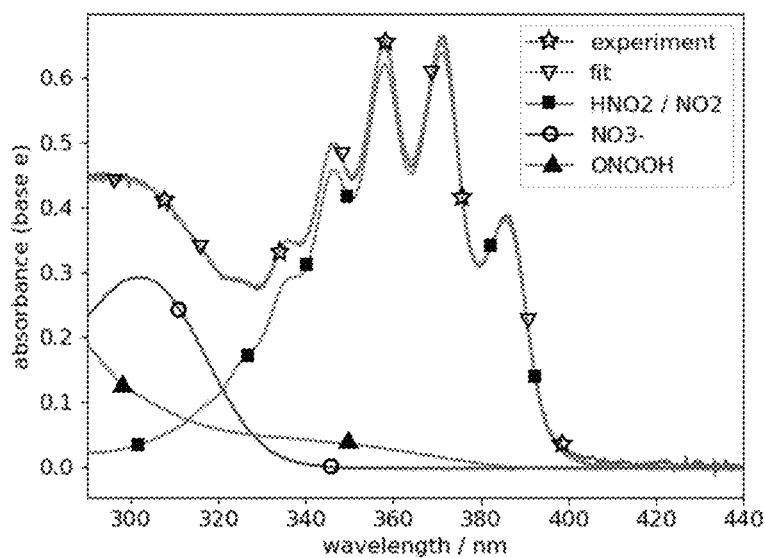
FIG. 20: Absorbance and fit at time t=20 s for the reaction of 73.2 mM $NaNO_2$, 58.9 mM $H_2O_2$ and 100 mM HCl at 0° C.

In another experiment the same starting solutions as described above ($NaNO_2$, $H_2O_2$, HCl) were used, which were also brought to a temperature of 0° C. in an ice bath. In this experiment, however, these were brought to reaction directly in a cuvette so that the reaction could be followed time-resolved. For this purpose, the $NaNO_2$ and HCl solutions were placed in the cuvette and the reaction started by adding HCl. The results of this measurement are shown in FIG. 19. In addition, FIG. 20 shows the measurement and the adapted model function with contributions of the species $NO_3^-$, ONOOH and $HNO_2/NO_2^-$. $HNO_2/NO_2^-$ is the total density of $HNO_2$ and $NO_2^-$. The effective cross section of the acid or the conjugated base was calculated in advance for pH 2.1. The effective cross section used for ONOOH was determined in our own preliminary work and is consistent with the effective cross section published in Loegager & Sehested (1993). The formation of ONOOH was thus also proven in the limit range of the method performed according to the invention (0° C., pH 2.1).

Efficacy Parameters for Different Microorganisms

Figure 21:
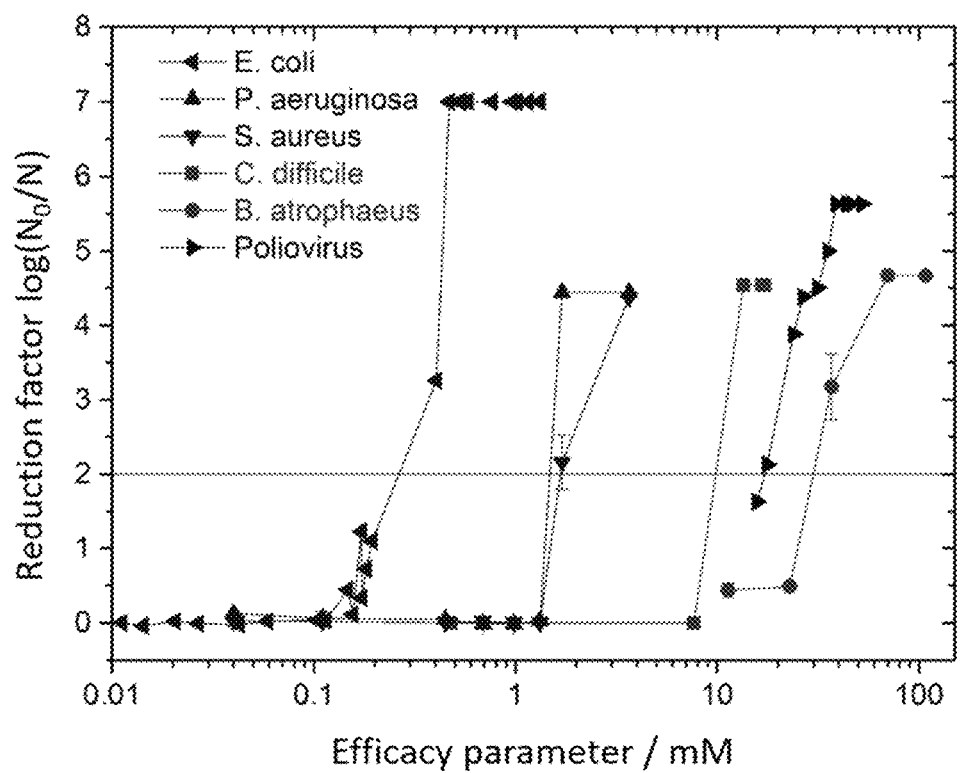
FIG. 21: Reduction factors for different types of microorganisms as a function of the efficacy parameter W. The horizontal line corresponds to a 99% reduction of the microorganism concentration.
Figure 22:
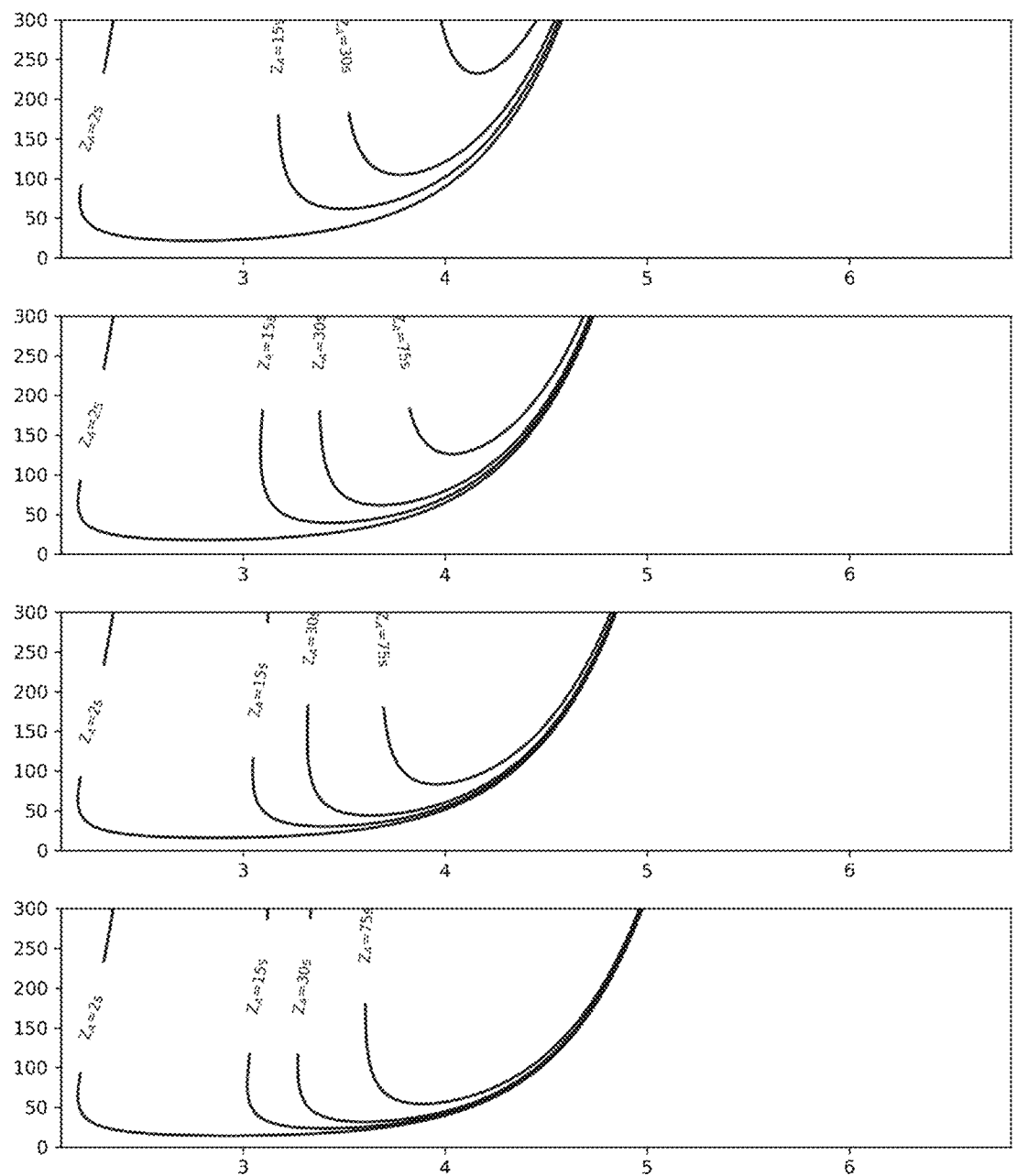
FIG. 22: Efficacy ranges at a temperature of 20° C. and exposure times $Z_E$ of 15 s, 30 s, 50 s and 90 s (from top to bottom). In the areas above the curves, W>10 mM applies to the efficacy parameter for the respective given duration of the processing period $Z_A$ selected from 2 s, 15 s, 30 s and 75. For x, the pH value is plotted and for y, the initial concentrations $[H_2O_2]_0=[NO_2^-]_0$ in mM.

The biological structure of different types of microorganisms is different. This suggests that not all microorganisms react in the same way to a disinfection method. In order to test the validity of the efficacy parameter for different categories of microorganisms, the effect of the method according to the invention was tested on vegetative and spore-forming bacteria as well as on non-enveloped viruses. In contrast to vegetative bacteria, bacterial spores and non-enveloped viruses cannot be inactivated with alcohol-based agents or only after an insufficiently long period of time. This resistance is also shown in the test results shown in FIG. 21. Already at an efficacy parameter of 0.3 mM 99% (2 log steps) of *Escherichia coli* bacteria in suspension are killed. Other species of the category "vegetative bacteria" such as *Pseudomonas aeruginosa* and *Staphylococcus aureus* require a slightly higher efficacy parameter of 1.5 mM and 1.7 mM, respectively, but these values are still significantly below the required efficacy parameters for bacterial spores. Here, an efficacy parameter of 10 mM is required for *Clostridium difficile* spores for 99% inactivation. The *Clostridium difficile* spore is of particular relevance, since it is the most common pathogen of nosocomial and antibiotic-associated diarrhea (Lübbert et al. 2014). More resistant spores like *Bacillus atrophaeus* require an efficacy parameter of 30 mM. For the third category "non-enveloped viruses" the disinfection performance was tested on poliovirus, which requires an efficacy parameter of 17.2 mM for 99% inactivation. The respective values are listed in Table 1 below for overview.

TABLE 1

Efficacy parameters for vegetative microorganisms, bacterial spores and non-enveloped viruses

| Species | Microorganism | necessary efficacy parameter for 2-log (99%) inactivation/mM | necessary efficacy parameter for 4-log (99.99%) inactivation/mM |
|---|---|---|---|
| vegetative microorganisms | E. coli | 0.3 | 0.42 |
| | P. aeruginosa | 1.5 | 1.62 |
| | S. aureus | 1.7 | 3.2 |
| bacterial spores | C. difficile | 10 | 12.7 |
| | B. atrophaeus | 30 | 52 |
| non-enveloped viruses | Poliovirus type 1 | 17.2 | 24.2 |

Efficacy Parameters for Different Microorganisms

In Heaselgrave 2010 microbiological inactivation experiments were performed for various microorganisms at the following parameters: pH=5, $[H_2O_2]_0$=171 mM and $[NO_2^-]_0$=29 mM.

Table 2 below shows the efficacy parameters W calculated from these parameters and the corresponding exposure time.

TABLE 2

Efficacy parameter W for the disinfectant according to Heaselgrave 2010 for an exposure time of 15 min or 60 min as well as for a processing and exposure time according to the invention ($Z_A$ = 2 s, $Z_E$ = 90 s).

| | Heaselgrave 2010 | | | |
|---|---|---|---|---|
| Microorganism | required exposure time for 4log reduction/s | calculated efficacy parameter for 4log reduction/mM | calculated efficacy parameters for $Z_A$ = 2 s, $Z_E$ = 90 s/mM | Efficiency with $Z_A$ = 2 s, $Z_E$ = 90 s/% |
| P. aeruginosa | 900 | 4.6 | 0.51 | 1.9 |
| S. aureus | 900 | 4.6 | 0.51 | 1.9 |
| B. subtilis Spores | 3600 | 14.2 | 0.51 | 1.9 |

For vegetative microorganisms such as *Pseudomonas aeruginosa* or *Staphylococcus aureus*, Heaselgrave et al. require efficacy parameters of 4.6 mM to achieve a reduction factor of 4 log levels. For bacterial spores, which are much more resistant, the required efficacy parameter is significantly higher. According to the experimental parameters of Heaselgrave et al. (2010), the efficacy parameter for *Bacillus subtilis* endospores is correspondingly calculated to 14.2 mM. In contrast to the disinfection method according to the invention, much longer periods of time (15 min and 60 min, respectively) are required to achieve the efficacy parameters of 4.6 mM and 14.2 mM.

The table also shows the efficacy parameters that would result from the parameters (pH, $C_{H2O2}$, $C_{NaNO2}$) used by Heaselgrave et al. (2010) at a processing time $Z_A$=2 s and an exposure time $Z_E$=90 s. Since the parameters were the same in all experiments, an identical efficacy parameter of 0.51 mM is obtained for all microorganisms shown. This is 9 times smaller for vegetative microorganisms and 28 times smaller for endospores than would be required for a reduction by 4 log steps. An inactivation of relevant microorganisms within 92 s is completely hopeless with the parameters chosen by Heaselgrave et al., although the $NaNO_2$ and $H_2O_2$ concentrations used by Heaselgrave et al. are already very high compared to the concentrations used in the invention. All other combinations of processing time and exposure time with the initial concentrations according to Heaselgrave et al. provide even lower efficacy parameters and thus increase the required factor to achieve a sufficient efficacy parameter.

Furthermore, the efficiency E=1.9% of the process by Heaselgrave et al. is extremely low for the considered period of 92 s. This means that for the processing and exposure time considered ($Z_A$=2 s, $Z_E$=90 s) the efficacy parameter achieved by Heaselgrave et al. corresponds to only 1.9% of the efficacy parameter that would theoretically be achievable with a favourable choice of pH and initial concentrations of $H_2O_2$ and $NO_2^-$. In addition to the better efficacy, against the background of an efficient use of raw materials, the method according to the invention is therefore also to be preferred to that of Heaselgrave et al. with regard to efficiency.

LIST OF REFERENCES

Anbar, M., & Taube, H. (1954). Interaction of Nitrous Acid with Hydrogen Peroxide and with Water. *Journal of the American Chemical Society*, 76(24), 6243-6247. https://doi.org/10.1021/ja01653a007

Damschen, D. E., & Martin, L. R. (1983). Aqueous aerosol oxidation of nitrous acid by O2, O3AND $H_2O_2$. *Atmospheric Environment* (1967), 17(10), 2005-2011. https://doi.org/10.1016/0004-6981(83)90357-8

E. Halfpenny, P. L. R. (1952). Pernitrous acid. The reaction between hydrogen peroxide and nitrous acid, and the properties of an intermediate product. *Journal of the Chemical Society* (Resumed), (0), 928-938.

Heaselgrave, W., Andrew, P. W., & Kilvington, S. (2010). Acidified nitrite enhances hydrogen peroxide disinfection of *Acanthamoeba*, bacteria and fungi. *Journal of Antimicrobial Chemotherapy*, 65(6), 1207-1214. https://doi.org/10.1093/jac/dkq075

Ikawa, S., Tani, A., Nakashima Y., Kitano K. (2016) Physicochemical properties of bactericidal plasma-treated water. *Journal of Physics D: Applied Physics*, 49, 425401.

Jiang, G., & Yuan, Z. (2013). Synergistic inactivation of anaerobic wastewater biofilm by free nitrous acid and hydrogen peroxide. *Journal of HaZ$_A$rdous Materials*, 250-251, 91-98. https://doi.org/10.1016/j.jhazmat.2013.01.047

Lammel G., Perner, D., Warneck, P. (1990) Decomposition of pernitric acid in aqueous solution. *Journal of Physical Chemistry*, 94, 6141.

Lee, Y.-N., & Lind, J. A. (1986). Kinetics of aqueous-phase oxidation of nitrogen(III) by hydrogen peroxide. *Journal of Geophysical Research*, 91(D2), 2793. https://doi.org/10.1029/JD091iDO2p02793

Loegager, T., & Sehested, K. (2005). Formation and decay of peroxynitric acid: a pulse radiolysis study. The Journal of Physical Chemistry, 97(39), 10047-10052

Loegager, T., & Sehested, K. (1993). Formation and decay of peroxynitrous acid: a pulse radiolysis study. *The Journal of Physical Chemistry*, 97(25), 6664-6669

Lübbert C, John E, von Müller L (2014) *Clostridium difficile* infection-guideline-based diagnosis and treatment. Deutsches Ärzteblatt International, 111, 723.

Lukes, P., DoleZ$_A$lova, E., Clupek, M., Jablonowski, H., Woedtke, T. Von, & Reuter, S. (2015). Kinetics of peroxynitrite formation and its decomposition in air plasma treated liquids, 5-8.

Szabo, J. G., Adcock, N. J., & Rice, E. W. (2014). Disinfection of *Bacillus* spores with acidified nitrite. *Chemosphere*, 113, 171-174. https://doi.org/10.1016/j.chemosphere.2014.05.038

Vione, D., Maurino, V., Minero, C., Borghesi, D., Lucchiari, M., & Pelizzetti, E. (2003). New processes in the environmental chemistry of nitrite. 2. The role of hydrogen peroxide. *Environmental Science and Technology*, 37(20), 4635-4641. https://doi.org/10.1021/es0300259

EP 1 715 057 "Planar device and method for generating a plasma or reactive species"

US 20170172149 "SteriliZ$_A$tion method, formulation for steriliZ$_A$tion use, and device for producing sterilizing liquid"

WO 2011134010 "Control of bacterial activity, such as in sewers and wastewater treatment systems"

We claim:

1. A disinfection method comprising contacting a surface with a peroxynitrous acid solution, the disinfection method comprising:

a mixing step at pH greater or equal to 2.1, wherein educts $H_2O_2$ and $NO_2^-$ are mixed to obtain a peroxynitrous acid solution, wherein no peroxinitrate is formed in the solution;

a distribution step in which the peroxynitrous acid solution is distributed on the surface to be disinfected, wherein the mixing step and the distribution step take place in a processing period $Z_A$ which begins at time $t_0$ when the educts are first brought into contact with one another and ends at time $t_1$ when each point on the surface to be disinfected is wetted with the peroxynitrous acid solution, wherein $t_0$ is equal to 0 and $t_1$ is greater than $t_0$, and subsequently an exposure step in which the distributed peroxynitrous acid solution acts on the surface contacted with the peroxynitrous acid solution over an exposure period $Z_e$ that begins at time $t_1$ and ends after time period $Z_e$ at time $t_2$, wherein $t_2$ represents the time at which each point on the surface contacted with the peroxynitrous acid solution is wetted with the peroxynitrous acid solution for a sufficient time to obtain a disinfecting effect, and wherein $t_2$ is greater than $t_1$, characterized in that the educts $NO_2^-$ and $H_2O_2$ are consumed in the ratio 1:1 to form ONOOH, the maximum $NO_2^-$ concentration $[NO_2^-]_0$ at time to of the mixing step is 300 mM, the time-dependent concentrations of the educts $[H_2O_2]$ and $[NO_2^-]$ during the processing period and the exposure period are given by $$[NO_2^-] = \frac{A}{k_1} \text{ and } [H_2O_2] = \frac{A+D}{k_1+rk_1}, \text{ wherein}$$

$$A = -\frac{D}{1-\exp(D(t-C))}, C = -\frac{\ln\left(\frac{D}{[NO_2^-]_0 \cdot k_1}+1\right)}{D},$$

$$D = [H_2O_2]_0 \cdot (k_1+rk_1) - [NO_2^-]_0 \cdot k_1,$$

$$k_1 = k_4 \frac{[H_3O^+]^2}{(K_{S,H_3O_2^+}+[H_3O^+])(K_{S,HNO_2}+[H_3O^+])},$$

$$k_4 = 3.56 \cdot 10^{14} \exp\left(-\frac{E_A}{RT}\right) M^{-1} s^{-1},$$

$$K_{S,HNO_2} = 5.13 \times 10^{-4},$$

$$K_{S,H_3O_2^+} = 2 \times 10^{-2}, [H_3O^+] = 10^{-pH}, E_A = 70 \text{ kJ/mol}$$

and $[H_2O_2]_0$ is the initial $H_2O_2$ concentration at time $t_0$ of the mixing step and wherein r=0,11 is to be set, and the time-integrated reaction rate W over the exposure period $Z_e$ fulfills the inequality $$W = \int_{t_1}^{t_2} k_1 \cdot [H_2O_2] \cdot [NO_2^-] dt \geq 10 \text{ mM},$$

wherein $t_2$ does not exceed 3 minutes, and wherein k1 is the pH-dependent rate constant of the reaction between $H_2O_2$ and $NO_2^-$, and wherein the pH of the peroxynitrous acid solution prior to contact with the surface to be disinfected is in the range of 2.1≤pH<6.8, and wherein pH value of the peroxynitrous acid solution is always greater than or equal to 2.1 before and during the distribution and exposure times.

2. The disinfection method according to claim 1, wherein the processing period, which ends at time $t_1$, is selected from the range $0 < t_1 \leq 30$ s.

3. The disinfection method according to claim 1, wherein the exposure period, which begins at time $t_1$ and ends at time $t_2$, is a maximum of 50 s.

4. The disinfection method according to claim 1, wherein the pH of the peroxynitrous acid solution that is contacting the surface is in the range of $2.1 \leq pH < 6.8$.

5. The disinfection method according to claim 1, wherein the pH of the peroxynitrous acid solution prior to contact with the surface to be disinfected is in the range of 2.1 to 4.5.

6. The disinfection method according to claim 1, wherein the maximum initial concentration of $NO_2^-$ at time $t_0$ does not exceed a concentration of 200 mM.

7. The disinfection method according to claim 1, wherein the efficiency $E = W/W_{max}$ is at least 10%, wherein $$W_{max} = \min([H_2O_2]_0, [NO_2^-]_0)(\exp(-Gt_1) - \exp(-Gt_2))$$

with $$G = \ln\left(\frac{t_2}{t_1}\right) / (t_2 - t_1)$$

designates the maximum achievable efficacy parameter at given times $t_2$ and $t_1$ and $\min([H_2O_2]_0, [NO_2^-]_0)$ designates the minimum concentration selected from the initial concentrations $[H_2O_2]_0$ and $[NO_2^-]_0$.

8. The disinfection method according to claim 1, wherein additives in form of acid buffers and acid buffer solutions, respectively, are added to the educts and/or the peroxynitrous acid solution.

9. The disinfection method according to claim 1, wherein the surface is disinfected by the method several times.

10. The disinfection method according to claim 1, wherein the surface is skin and/or the composition is distributed on a wound.

* * * * *